United States Patent
Yada et al.

(10) Patent No.: US 10,172,806 B2
(45) Date of Patent: Jan. 8, 2019

(54) PHARMACEUTICAL COMPOSITION HAVING ABUSE DETERRENT PROPERTIES

(71) Applicant: Daiichi Sankyo Company, Limited, Chuo-ku, Tokyo (JP)

(72) Inventors: Shuichi Yada, Fujisawa (JP); Ryoichi Hayakawa, Yokohama (JP); Atsutoshi Ito, Ota-ku (JP); Hideki Yano, Fujisawa (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

(21) Appl. No.: 15/622,714

(22) Filed: Jun. 14, 2017

(65) Prior Publication Data

US 2017/0273975 A1    Sep. 28, 2017

Related U.S. Application Data

(63) Continuation of application No. PCT/JP2016/069190, filed on Jun. 29, 2016.

(30) Foreign Application Priority Data

Jun. 30, 2015  (JP) ................ 2015-130840

(51) Int. Cl.
*A61K 31/485*  (2006.01)
*A61K 31/135*  (2006.01)
(Continued)

(52) U.S. Cl.
CPC .......... *A61K 9/5084* (2013.01); *A61K 9/0019* (2013.01); *A61K 9/0053* (2013.01);
(Continued)

(58) Field of Classification Search
None
See application file for complete search history.

(56) References Cited

U.S. PATENT DOCUMENTS

| 4,331,445 A * | 5/1982 | Burns ............... C10L 9/10 44/501 |
| 6,602,995 B2 * | 8/2003 | Maruyama ......... C08B 11/08 536/124 |

(Continued)

FOREIGN PATENT DOCUMENTS

| JP | 2008-529990 A | 8/2008 |
| JP | 2015-514733 A | 5/2015 |
| WO | 2013/156453 A1 | 10/2013 |

OTHER PUBLICATIONS

International Search Report and Written Opinion dated Sep. 20, 2016, issued in corresponding International Application No. PCT/JP2016/069190, filed Jun. 29 2016, 19 pages.

(Continued)

*Primary Examiner* — Bethany P Barham
*Assistant Examiner* — Dominic Lazaro
(74) *Attorney, Agent, or Firm* — Christenson O'Connor Johnson Kindness PLLC

(57) ABSTRACT

An object of the present invention is to provide a pharmaceutical composition having abuse deterrent properties and thereby prevent the abuse of a pharmacologically active component by an abuser (abuse through snorting, abuse through injection, or abuse through snorting or injection of a temporarily extracted drug). The present invention provides a pharmaceutical composition having abuse deterrent properties that possesses both a physical barrier and a chemical barrier to being abused by an abuser, a method for producing the same and a method for using the same.

30 Claims, 6 Drawing Sheets

(51) Int. Cl.
- *A61K 31/194* (2006.01)
- *A61K 9/08* (2006.01)
- *A61K 9/20* (2006.01)
- *A61K 9/00* (2006.01)
- *A61K 9/50* (2006.01)
- *A61K 9/14* (2006.01)
- *A61K 47/14* (2017.01)
- *A61K 47/32* (2006.01)
- *A61K 47/34* (2017.01)
- *A61K 47/36* (2006.01)
- *A61K 47/38* (2006.01)

(52) U.S. Cl.
CPC ............... *A61K 9/08* (2013.01); *A61K 9/14* (2013.01); *A61K 9/141* (2013.01); *A61K 9/20* (2013.01); *A61K 9/204* (2013.01); *A61K 9/2013* (2013.01); *A61K 9/2054* (2013.01); *A61K 31/135* (2013.01); *A61K 31/194* (2013.01); *A61K 31/485* (2013.01); *A61K 47/14* (2013.01); *A61K 47/32* (2013.01); *A61K 47/34* (2013.01); *A61K 47/36* (2013.01); *A61K 47/38* (2013.01)

(56) References Cited

U.S. PATENT DOCUMENTS

| | | | |
|---|---|---|---|
| 6,605,302 | B2* | 8/2003 | Faour ............... A61K 9/0004 424/473 |
| 2003/0068375 | A1 | 4/2003 | Wright et al. |
| 2006/0051298 | A1 | 3/2006 | Groenewoud |
| 2009/0041831 | A1* | 2/2009 | Miller, II ............ A61K 9/7069 424/448 |
| 2009/0041838 | A1 | 2/2009 | Guimberteau et al. |
| 2010/0021549 | A1* | 1/2010 | Meyrueix ............... A61K 8/11 514/1.1 |
| 2010/0266701 | A1 | 10/2010 | Guimberteau et al. |
| 2013/0028972 | A1 | 1/2013 | Schwier et al. |
| 2013/0280338 | A1 | 10/2013 | Wening et al. |
| 2013/0281388 | A1* | 10/2013 | Deaver ............... A61K 31/485 514/27 |

OTHER PUBLICATIONS

Extended European Search Report dated Dec. 20, 2017, issued in corresponding Application No. EP 16817937.2, filed Jun. 29, 2016, 8 pages.

* cited by examiner

[Figure 1]
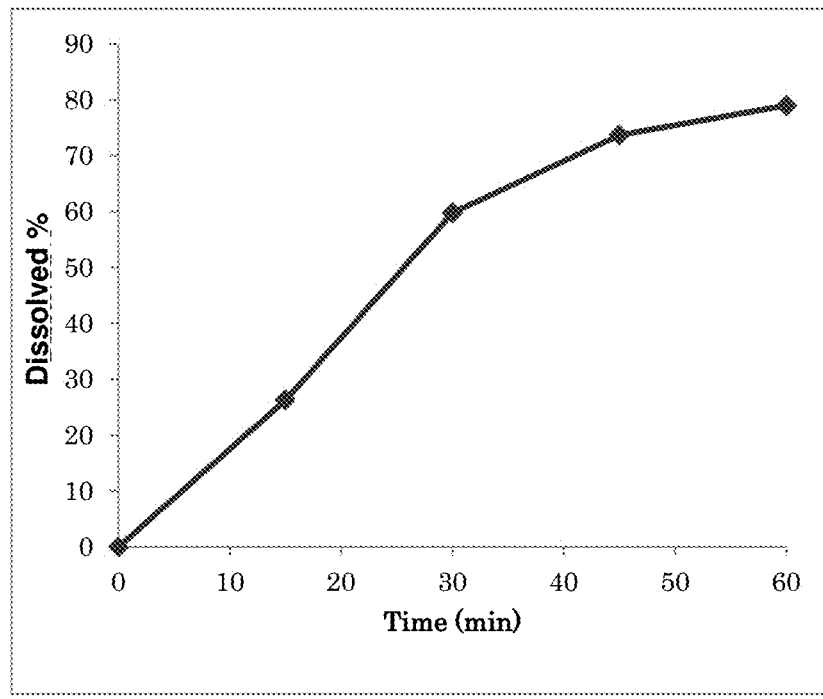
[Figure 2]
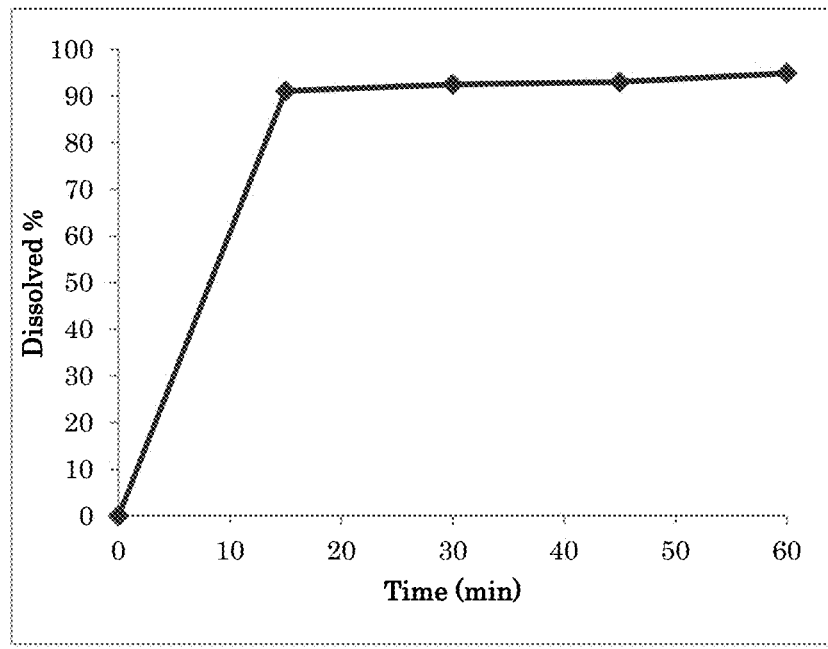

[Figure 3]
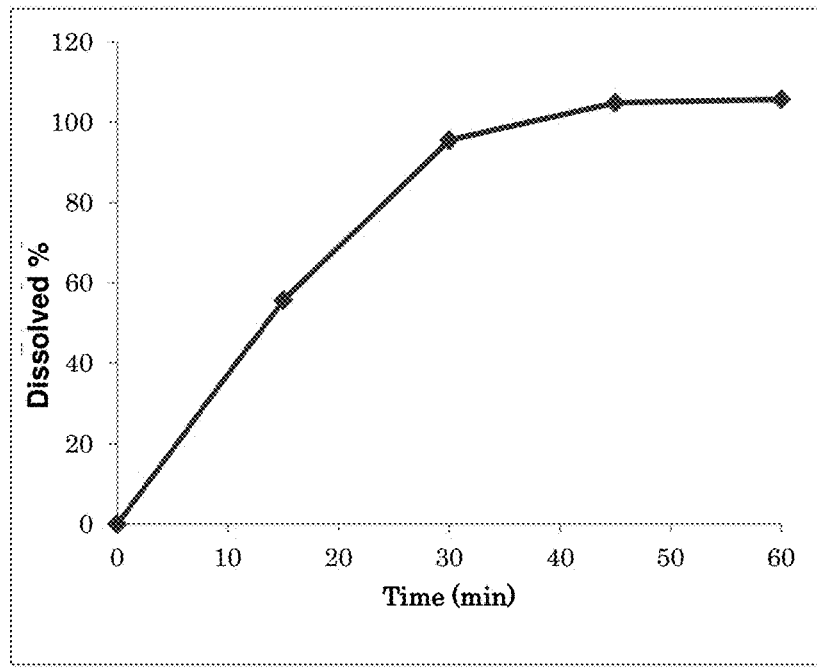
[Figure 4]
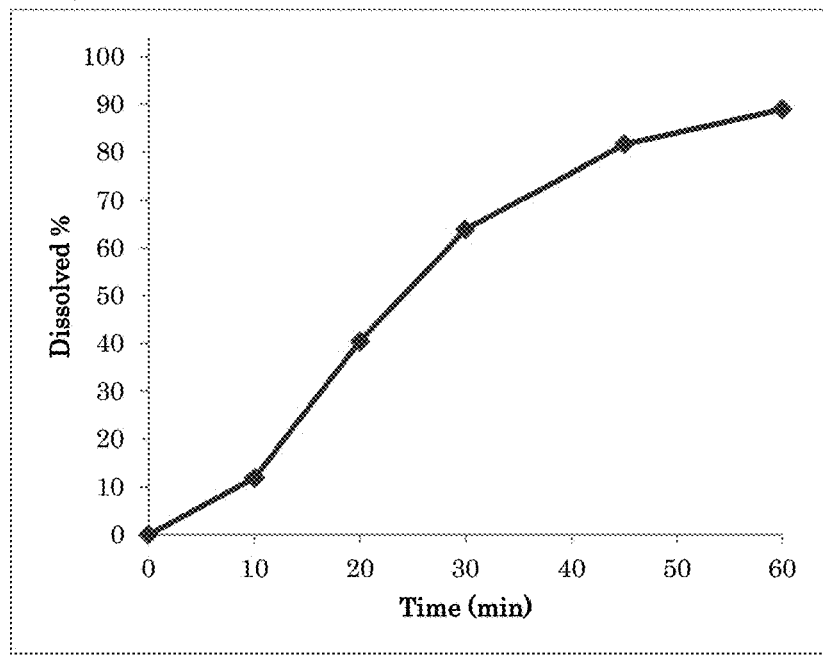

[Figure 5]
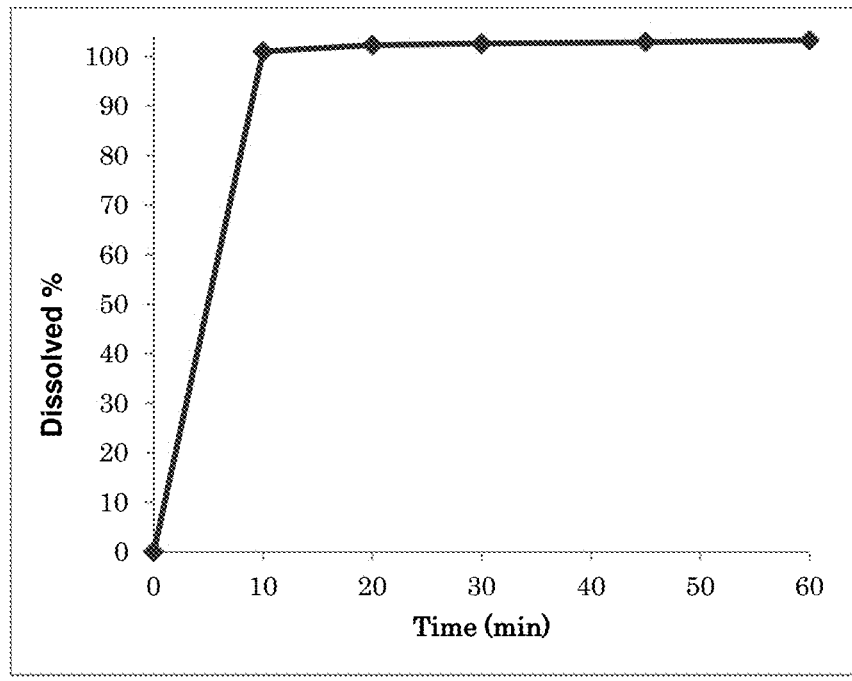
[Figure 6]
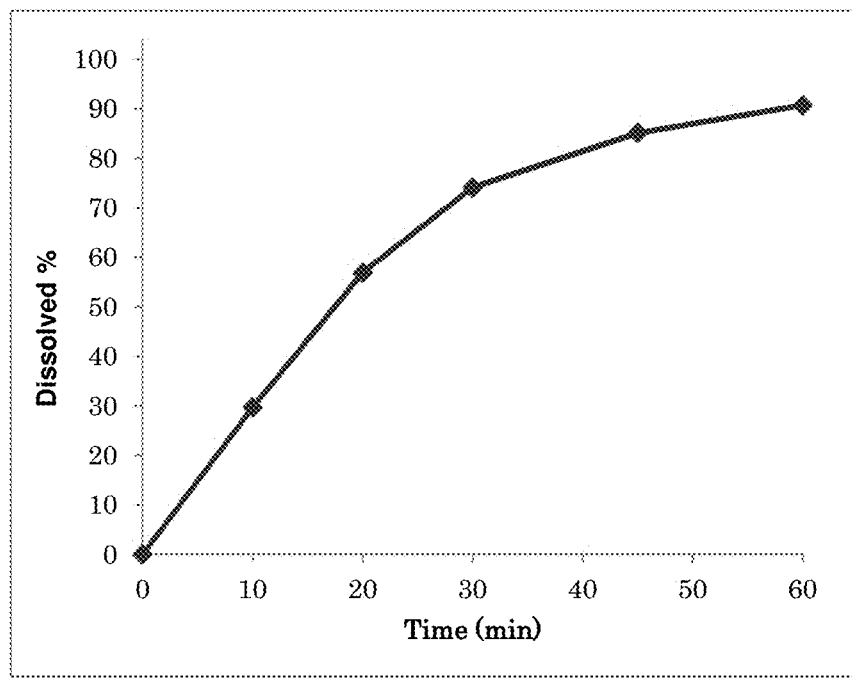

[Figure 7]
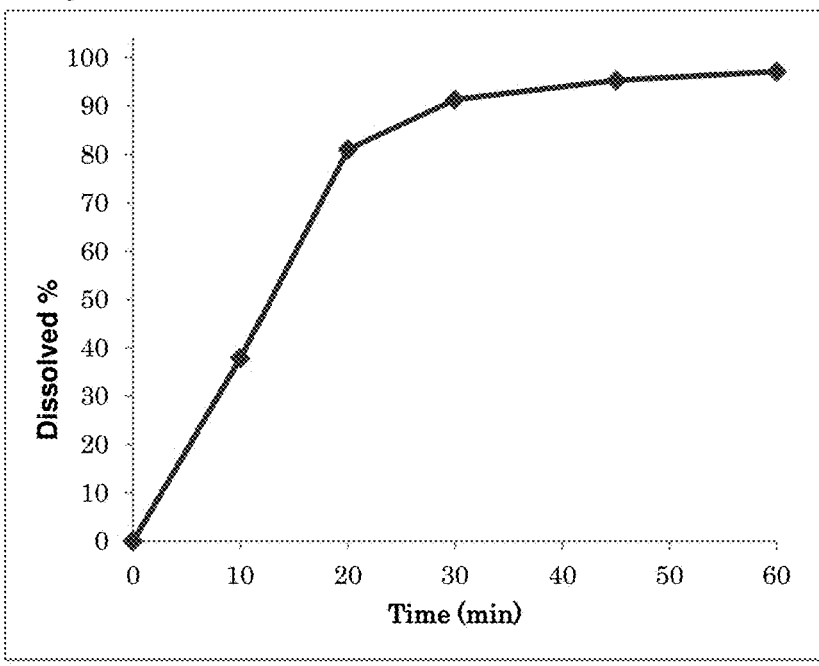
[Figure 8]
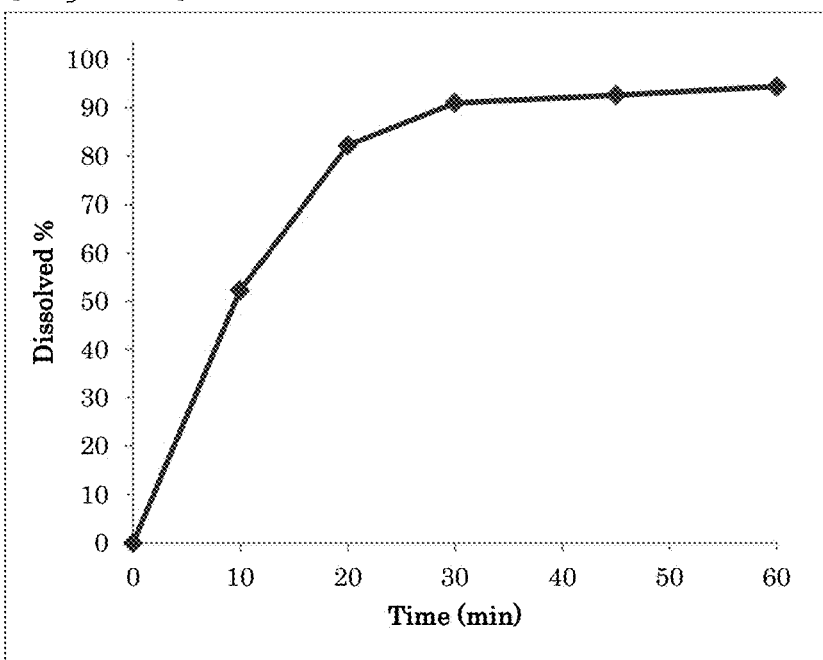

[Figure 9]
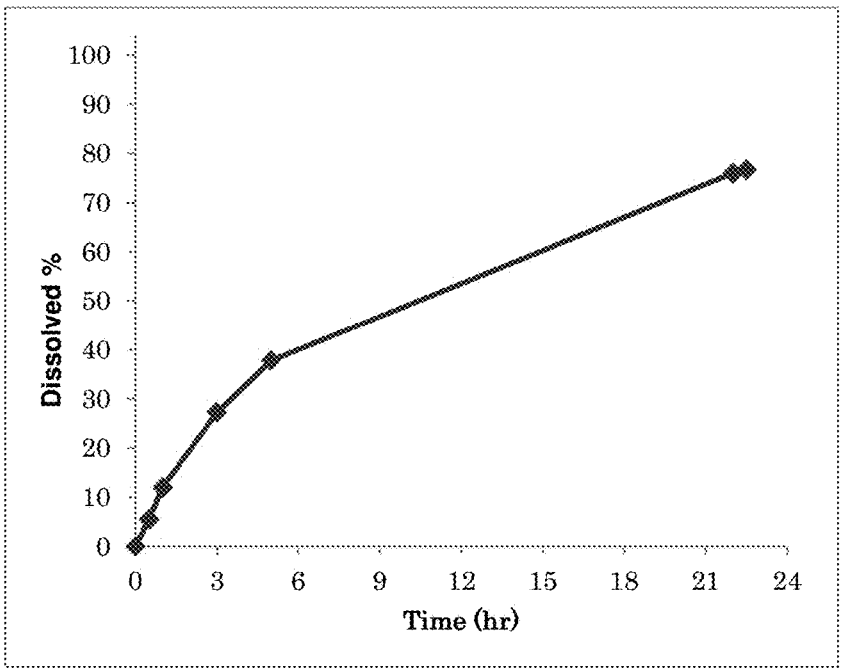
[Figure 10]
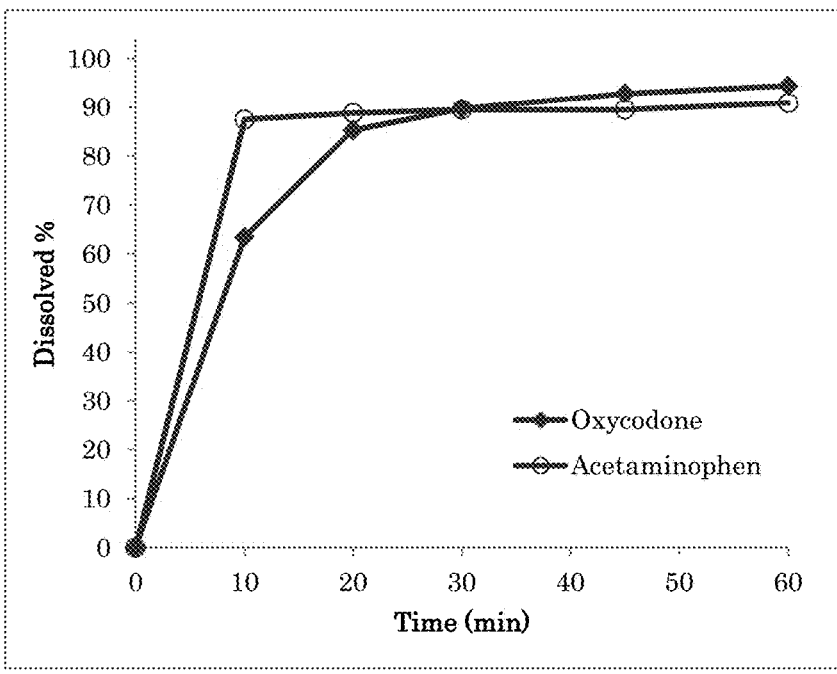

[Figure 11]
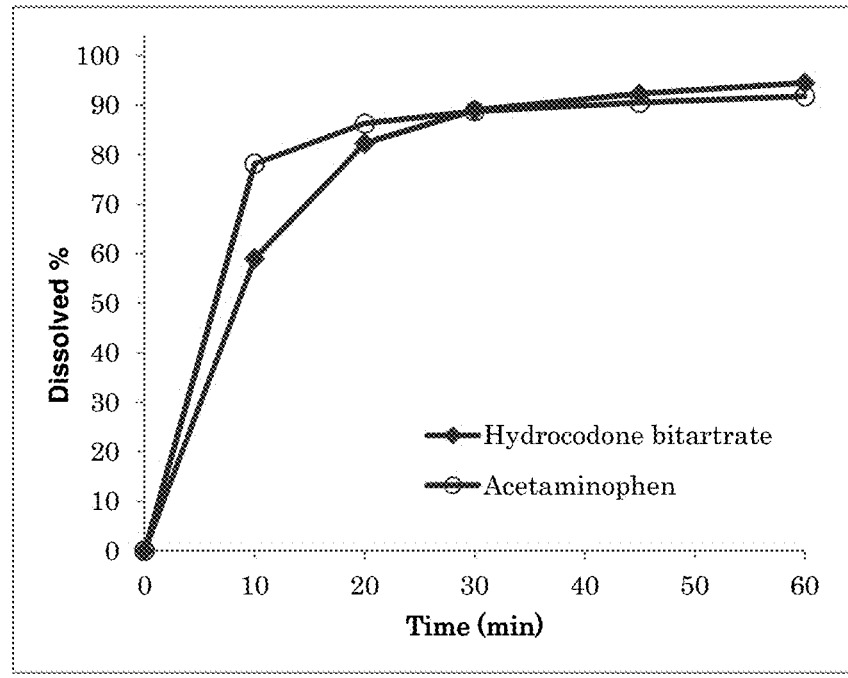
[Figure 12]
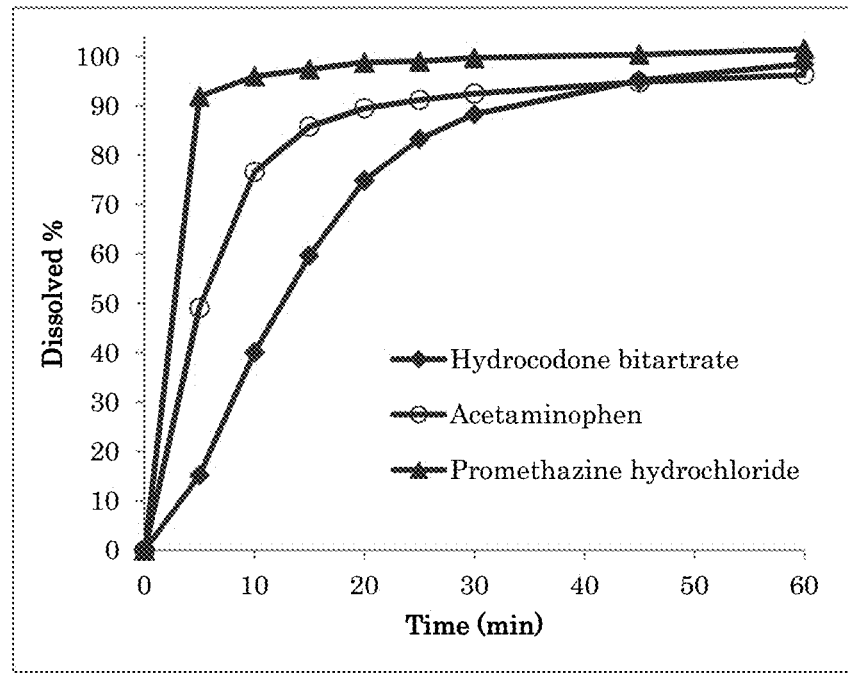

PHARMACEUTICAL COMPOSITION HAVING ABUSE DETERRENT PROPERTIES

CROSS-REFERENCES TO RELATED APPLICATIONS

This application is a continuation of International Application No. PCT/JP2016/069190, filed Jun. 29, 2016, which claims the benefit of Japanese Application No. 2015-130840, filed Jun. 30, 2015.

TECHNICAL FIELD

The present invention relates to a pharmaceutical composition containing a pharmacologically active compound and having abuse deterrent properties.

BACKGROUND ART

Most pharmacologically active substances may be used for bringing about effects incompatible with their originally intended usage. In short, pharmacologically active substances such as narcotic analgesics, opioid analgesics or psychotropics for use in cancer pain are abused or wrongfully used, and not properly used for the treatment of diseases. For example, opioids which are highly effective for controlling severe pain are often abused to induce a state of high similar to drunkenness. In the worst case, persons who have abused opioid may die as a result.

Persons who attempt to abuse a pharmacologically active substance (abusers) employ various methods in order to be able to abuse the substance. For example, abusers can obtain the desired result, i.e., a drunk-like high, by ingesting a powder obtained by the crushing or grinding of tablets or capsules through the mouth or by snorting the powder through the nose. Alternatively, abusers extract a pharmacologically active substance via an aqueous liquid from a powder obtained by the grinding of tablets or capsules and can obtain a drunk-like high by parenterally, particularly, intravenously, administering the obtained solution. In an alternative possible approach, abusers extract a pharmacologically active substance not only into ethanol but into various organic solvents, then dissolve, in an aqueous liquid, a powder after evaporating the organic solvent and then inject the resulting solution, or directly snort the powder through the nose.

The abuse of pharmacologically active substances is now becoming a very serious social problem in the United States. The Food and Drug Administration (FDA) issued Abuse-Deterrent Opioids—Evaluation and Labeling as Guidance for Industry in April 2015 in order to prevent the abuse of pharmaceutical products. This guidance describes various approaches for avoiding drug abuse.

For example, it has been proposed that formulations containing a harmful agent or antagonist in addition to a pharmacologically active substance are designed to bring about unpleasant effects or antagonistic effects only when misapplied. Another example includes the avoidance of drug abuse by enhancing the mechanical properties, particularly, mechanical strength, of formulations. The main advantage of such formulations is that it is impossible to crush the formulations into powder by ordinary means used by abusers, for example, grinding in a mortar or pulverization using a hammer, or the formulations are at least unable to be injected or are substantially hindered from being snorted through the nose.

The challenge for extended-release formulations containing opioids is to render the formulations unable to be pulverized for abuse but to produce adequate therapeutic effects when properly used. According to WO2006/002884 (Patent Literature 1), it has been found that an extended-release formulation containing opioids, a synthetic or natural polymer and wax has a fracture resistance (mechanical strength) that renders the formulation unable to be pulverized. According to this invention, the mechanical strength of the extended-release formulation produced through the use of the properties of the polymer (polyethylene oxide) is too large for abusers to be able to pulverize the formulation. Thus, it is impossible for abusers to chew up and swallow the formulation or to snort the formulation through the nose. In addition, the polymer (polyethylene oxide) used has a property of exhibiting a high viscosity upon contact with water. Therefore, abusers cannot inject the solution because the solution cannot be aspirated into a syringe.

Formulations that must resist being abused are not limited to the extended-release formulations. In short, the challenge for attempts to obtain analgesic effects especially rapidly by proper use is that immediate release of the pharmacologically active substance is required. WO2013/017242 (Patent Literature 2) discloses an invention relating to an abuse deterrent formulation comprising a matrix material and a plurality of particulates, the particulates comprising a pharmacologically active substance and a polyalkylene oxide, wherein the particulates are embedded in the matrix material to form a discontinuous phase. According to this invention, rapid pharmacological effects are expected because the pharmacologically active substance is immediately released from the formulation. Furthermore, snorting is impossible because the particulates have adequate mechanical strength and are thus not pulverized. In addition, the polymer (polyethylene oxide) used has a property of exhibiting a high viscosity upon contact with water. Therefore, abusers cannot inject the solution because the solution cannot be aspirated into a syringe.

Likewise, according to National Publication of International Patent Application No. 2008-520634 (Patent Literature 3), granules comprising thickener-containing fine particles supplemented with a wax having a low melting point have a property of exhibiting a high viscosity upon contact with water. Therefore, abusers cannot inject the solution. Furthermore, the granules become a paste even if pulverized. Therefore, abusers cannot snort the paste through the nose.

National Publication of International Patent Application No. 2009-537456 (Patent Literature 4) discloses an invention relating to an extended-release formulation in which granules containing a pharmacologically active substance are provided with a coating for controlling the release of the pharmacologically active substance and coexist with a thickener and an ion-exchange resin. According to this invention, the dissolution behavior of the pharmacologically active substance does not change between before and after pulverization even if the granules are pulverized. Thus, the thickener and the ion-exchange resin can prevent the pharmacologically active substance in the granules from being liberated into water, alcoholic drinks or nonalcoholic drinks.

However, these preceding techniques are not satisfactory in terms of the following points.

In WO2006/002884 (Patent Literature 1), the manufacture of an extended-release formulation having adequate mechanical strength requires special manufacturing apparatus because of the properties of polyethylene oxide used. Therefore, this approach is not versatile. Polyethylene oxide, which is commonly used in WO2006/002884 (Patent Literature 1) and WO2013/017242 (Patent Literature 2), produces tablets or granules having mechanical strength (flexibility) by the application of a temperature equal to or higher than the softening point because of its material properties and can provide a formulation having abuse deterrent properties. However, polyethylene oxide is a heat-labile substance in the first place. Thus, not only is polyethylene oxide itself decomposed thereby decreasing its functions, but the decomposition product reacts compositely with the pharmacologically active substance so that the pharmacologically active substance is decomposed (Non-patent Literatures 1 and 2). Therefore, a manufacturing method using a heating process (hot melt extrusion method) is not always the best method.

In the case of adopting the hot melt extrusion method, a stabilizer such as α-tocopherol or dibutylhydroxytoluene may be used for stabilizing polyethylene oxide. However, the cost and time for development are increased because the appropriate amount and safety of the stabilizer, the stability of the pharmaceutical product, and the influence on pharmaceutical additives having other functions are to be confirmed (Non-patent Literatures 3 and 4).

National Publication of International Patent Application No. 2008-520634 (Patent Literature 3) does not specifically disclose a release rate related to effectiveness or safety. Therefore, it is not certain that effectiveness or safety can be secured by proper use.

In an alternative possible approach of abuse, abusers employ not only ethanol but various organic solvents, particularly, in the extraction of pharmacologically active substances, then dissolve, in an aqueous liquid, a powder after evaporation of the organic solvents and inject the resulting solution, or directly snort the powder through the nose. Polyethylene oxide, which is used in WO2006/002884 (Patent Literature 1) and WO2013/017242 (Patent Literature 2), has a property of having affinity for water and exhibiting a high viscosity in water and is therefore a pharmaceutical additive suitable for the development of abuse deterrent formulations. However, extractability using organic solvents such as methanol is high for formulations produced by the hot melt extrusion method. Therefore, this approach lacks measures against the extraction of a pharmacologically active substance by abusers. The technique used in National Publication of International Patent Application No. 2009-537456 (Patent Literature 4) tempts abusers to extract a pharmacologically active substance using, for example, methanol or other organic solvents, and is thus not sufficient, because it is limited to water, ethanol, a mixed solvent thereof, and typically drinkable solutions, as solvents for extraction.

CITATION LIST

Patent Literature

Patent Literature 1: WO2006/002884
Patent Literature 2: WO2013/017242
Patent Literature 3: National Publication of International Patent Application No. 2008-520634
Patent Literature 4: National Publication of International Patent Application No. 2009-537456

Non-Patent Literature

Non-patent Literature 1: Oral Controlled Release Formulation Design and Drug Delivery, Hong Wen, Kinam Park, 2011
Non-patent Literature 2: Michael M. Crowley et al., Biomaterial 23, 4241-4248 (2002)
Non-patent Literature 3: Sridhar Thumma et al., European Journal of Pharmaceutics and Biopharmaceutics 70, 605-614 (2008)
Non-patent Literature 4: Controlled Release in Oral Drug Delivery, Clive G. Wilson, 2011

SUMMARY OF INVENTION

Technical Problem

An object of the present invention is to provide a pharmaceutical composition having abuse deterrent properties and thereby prevent the abuse of a pharmacologically active component (drug) by an abuser (abuse through nasal inhalation, abuse through injection, or abuse through nasal inhalation or injection of an extracted drug).

Solution to Problem

The present inventors have conducted diligent studies to attain the prevention of the abuse of a drug by an abuser (abuse through nasal inhalation, abuse through injection, or abuse through nasal inhalation or injection of an extracted drug) and consequently completed the present invention by finding a pharmaceutical composition having abuse deterrent properties that possesses both a physical barrier and a chemical barrier. Specifically, a pharmaceutical composition comprising drug-containing granules having mechanical strength yields a viscous solution upon contact with a water-containing solvent and thereby prevents the abuse by an abuser (abuse through nasal inhalation, abuse through injection, or abuse through snorting or injection of an extracted drug) through the use of its property of exhibiting extraction resistance by which the drug is not easily extracted using water-containing solvents, various organic solvents or mixed solvents thereof.

In the conventional way of using polyethylene oxide in abuse deterrent formulations, polyethylene oxide resides close to the drug, and an approach of applying a temperature equal to or higher than the softening point because of its material properties is adopted. As a result, more rigid tablets or granules having mechanical strength (flexibility) are formed, and abuse deterrent formulations can be provided. However, polyethylene oxide is a heat-labile substance. Thus, not only is polyethylene oxide itself decomposed to decrease its function, but the decomposition product presumably reacts compositely with the drug so that the drug is decomposed. Therefore, a manufacturing method using a heating process (hot melt extrusion method) is not always the best method. In addition, a method for producing tablets by the hot melt extrusion method requires special apparatus and is therefore not versatile.

In a further possible approach, polyethylene oxide is physically isolated from a drug. However, granules of polyethylene oxide produced by a manufacturing method without the use of a heating process, such as dry granulation, have been found to have low physical strength and be insufficient for abuse deterrent properties.

The present inventors have conducted diligent studies to solve these problems and consequently found that polyethylene oxide and a drug are contained in separate granules in order to easily secure the stability of the formulation, and the drug-containing granules are prepared as granules having mechanical strength (flexibility) by the addition of a water-soluble polymer (cellulose derivative) and a plasticizer and combined with the polyethylene oxide-containing granules, whereby the resulting pharmaceutical composition sufficiently exerts abuse deterrent properties. Further studies have revealed that tablets exhibit immediate disintegration by adding a hydrophobic additive to the granules of polyethylene oxide. As mentioned later, since the drug release unit of this formulation is a multiple unit, components that exhibit tablet disintegration have been prepared as granules such that the tablets disintegrate rapidly and disperse as granules after disintegration of tablets. The extractability of drug into various organic solvents, particularly, methanol, has been found to be high for formulations produced by the hot melt extrusion method using polyethylene oxide. The present inventors have discovered that in order to reduce the extractability into organic solvents, extraction resistance to various organic solvents is obtained by combination with a water-soluble polymer in the present invention.

In order to obtain appropriate therapeutic effects (rapid therapeutic effects or sustained therapeutic effects), the dissolution rate from the formulation must be adjusted or controlled according to the properties of the drug. A multiple unit, not a single unit, has been selected as the drug release unit from the viewpoint of the easy adjustment or control of the dissolution rate and the easy conferring of abuse deterrent properties. It has actually been found that the dissolution rate from the multiple unit can be adjusted or controlled according to the present invention. Specifically, the present inventors have been completed the present invention by finding that the present invention allows for adjustment or control of drug release from a pharmaceutical composition, and a pharmaceutical composition is obtained as a formulation that confers abuse deterrent properties.

The present invention provides a pharmaceutical composition having abuse deterrent properties that possesses both a physical barrier and a chemical barrier to being abused by an abuser, a method for producing the same and a method for using the same.

Specifically, the present invention relates to the following:
(1) An abuse deterrent formulation that resists being abused by an abuser, the abuse deterrent formulation comprising at least 3 types of granules (A) to (C):
  (A) granules comprising a pharmacologically active drug, a cellulosic polymer and a plasticizer, the granules having a property of having mechanical strength against pulverization;
  (B) granules comprising a component that exhibits viscosity after dispersion in an aqueous solution; and
  (C) granules comprising a component that disintegrates the formulation.
(2) The abuse deterrent formulation according to (1), wherein the cellulosic polymer is hypromellose acetate succinate, ethylcellulose or hypromellose phthalate, and the plasticizer is triethyl citrate or triacetin.
(3) The abuse deterrent formulation according to (1) or (2), wherein the component that exhibits viscosity is a water-soluble polymer whose viscosity is not influenced by ionic strength.
(4) The abuse deterrent formulation according to (3), wherein the water-soluble polymer whose viscosity is not influenced by ionic strength is one or more members selected from hydroxypropylcellulose, hypromellose, polyvinyl alcohol, xanthan gum, guar gum, pectin and polyethylene oxide.
(5) The abuse deterrent formulation according to (3), wherein the water-soluble polymer whose viscosity is not influenced by ionic strength is polyethylene oxide.
(6) The abuse deterrent formulation according to any one of (1) to (5), wherein the granules (B) further comprise a hydrophobic additive that promotes the disintegration of tablets.
(7) The abuse deterrent formulation according to (6), wherein the hydrophobic additive is ethylcellulose.
(8) The abuse deterrent formulation according to any one of (1) to (7), wherein the component that disintegrates the formulation is a disintegrant.
(9) The abuse deterrent formulation according to (8), wherein the disintegrant is low-substituted hydroxypropylcellulose.
(10) The abuse deterrent formulation according to any one of (1) to (9), wherein the formulation further comprises a semi-natural water-soluble polymer.
(11) The abuse deterrent formulation according to (10), wherein the semi-natural water-soluble polymer is sodium carboxymethylcellulose.
(12) The abuse deterrent formulation according to any one of (1) to (11), wherein the formulation further comprises a polymer that exhibits viscosity when dissolved in an organic solvent.
(13) The abuse deterrent formulation according to (12), wherein the polymer that exhibits viscosity when dissolved in an organic solvent is hydroxypropylcellulose.
(14) The abuse deterrent formulation according to any one of (1) to (13), wherein the pharmacologically active drug is a narcotic analgesic, an opioid analgesic or a psychotropic.
(15) The abuse deterrent formulation according to any one of (1) to (13), wherein the pharmacologically active drug is hydromorphone or a salt thereof, hydrocodone or a salt thereof, oxycodone or a salt thereof, or tramadol or a salt thereof.
(16) The abuse deterrent formulation according to any one of (1) to (15), wherein the dosage form is an oral solid dosage form.
(17) The abuse deterrent formulation according to any one of (1) to (15), wherein the dosage form is a tablet.
(18) The abuse deterrent formulation according to (17), wherein the formulation exhibits immediate release.
(19) The abuse deterrent formulation according to (17), wherein the formulation exhibits extended release.
(20) The abuse deterrent formulation according to (19), wherein the formulation comprises the granules (A) provided with a coating.
(21) The abuse deterrent formulation according to (20), wherein the coating is made of a coating base composed mainly of ethylcellulose.
(22) A manufacturing method for obtaining an abuse deterrent formulation according to any one of (1) to (21), comprising separately manufacturing granules (A) comprising a pharmacologically active drug and granules (B) comprising polyethylene oxide and compression-molding a mixed powder containing these granules.
(23) The manufacturing method according to (22), further comprising a non-heating process for manufacturing the granules (B).
(24) The abuse deterrent formulation according to any one of (1) to (21) for use in a method for treating or preventing cancer pain or psychiatric disease.

Advantageous Effects of Invention

The present invention can provide a pharmaceutical composition having abuse deterrent properties that possesses both a physical barrier and a chemical barrier and thereby prevent abuse by an abuser.

BRIEF DESCRIPTION OF DRAWINGS

FIG. 1 is a diagram showing the dissolution of a tablet of Formulation Example 24 (test method: paddle method, test medium: water, amount of test medium: 500 mL, paddle rotation speed: 50 rpm).

FIG. 2 is a diagram showing the dissolution of a tablet of Formulation Example 25 (test method: paddle method, test medium: water, amount of test medium: 500 mL, paddle rotation speed: 50 rpm).

FIG. 3 is a diagram showing the dissolution of a tablet of Formulation Example 26 (test method: paddle method, test medium: 0.1 N hydrochloric acid, amount of test medium: 900 mL, paddle rotation speed: 100 rpm).

FIG. 4 is a diagram showing the dissolution of a tablet of Formulation Example 24 (test method: paddle method, test medium: 0.01 N hydrochloric acid, amount of test medium: 900 mL, paddle rotation speed: 50 rpm).

FIG. 5 is a diagram showing the dissolution of a tablet of Formulation Example 25 (test method: paddle method, test medium: 0.01 N hydrochloric acid, amount of test medium: 900 mL, paddle rotation speed: 50 rpm).

FIG. 6 is a diagram showing the dissolution of a tablet of Formulation Example 13 (test method: paddle method, test medium: 0.01 N hydrochloric acid, amount of test medium: 900 mL, paddle rotation speed: 50 rpm).

FIG. 7 is a diagram showing the dissolution of a tablet of Formulation Example 22 (test method: paddle method, test medium: 0.01 N hydrochloric acid, amount of test medium: 900 mL, paddle rotation speed: 50 rpm).

FIG. 8 is a diagram showing the dissolution of a tablet of Formulation Example 27 (test method: paddle method, test medium: 0.01 N hydrochloric acid, amount of test medium: 900 mL, paddle rotation speed: 50 rpm).

FIG. 9 is a diagram showing the dissolution of a tablet of Formulation Example 28 (test method: paddle method, test medium: Japanese Pharmacopoeia 2nd fluid for dissolution test, amount of test medium: 900 mL, paddle rotation speed: 50 rpm).

FIG. 10 is a diagram showing the dissolution of a tablet of Formulation Example 29 (test method: paddle method, test medium: 0.01 N hydrochloric acid, amount of test medium: 900 mL, paddle rotation speed: 50 rpm).

FIG. 11 is a diagram showing the dissolution of a tablet of Formulation Example 14 (test method: paddle method, test medium: 0.01 N hydrochloric acid, amount of test medium: 900 mL, paddle rotation speed: 50 rpm).

FIG. 12 is a diagram showing the dissolution of a tablet of Formulation Example 30 (test method: paddle method, test medium: 0.01 N hydrochloric acid, amount of test medium: 900 mL, paddle rotation speed: 50 rpm).

DESCRIPTION OF EMBODIMENTS

The cellulosic polymer contained in the granules (A) exhibits a flexible structural property by interaction with a plasticizer. Specifically, the cellulosic polymer is hypromellose acetate succinate, hypromellose phthalate, ethylcellulose or hypromellose.

The plasticizer is used for allowing the polymer used to assume a flexible structure by interaction with the polymer, and can be combined therewith according to the properties of the cellulose derivative used. Specifically, the plasticizer is triethyl citrate, triacetin or propylene carbonate.

The ratio between the cellulosic polymer and the plasticizer contained in the granules (A) is not limited as long as the resulting granules have adequate mechanical strength. In the case of, for example, hypromellose acetate succinate and triethyl citrate, the % by weight of triethyl citrate with respect to hypromellose acetate succinate contained in the granules except for the amount of triethyl citrate, if any, contained in a coating layer of the granules is 1% to 70%, preferably 2% to 60%, more preferably 3% to 50%.

The mechanical strength of the granules (A) is preferably large enough to leave granules having a particle size of 150 μm or larger when the granules are pulverized.

The water-soluble polymer whose viscosity is not influenced by ionic strength exhibits a property in which the viscosity is not influenced by ionic strength such that the viscosity of the water-soluble polymer in, for example, saline, is equivalent to that in water. Specifically, the water-soluble polymer whose viscosity is not influenced by ionic strength is hydroxypropylcellulose, hypromellose, polyvinyl alcohol, xanthan gum, guar gum, pectin and/or polyethylene oxide, preferably polyethylene oxide.

The component that exhibits viscosity after dispersion in an aqueous solution refers to a component that exhibits viscosity upon contact with water, saline or a generally drinkable liquid, and is mostly a water-soluble polymer. Specifically, the component that exhibits viscosity after dispersion in an aqueous solution is a component whose viscosity is not influenced by ionic strength in an aqueous solution, such as hydroxypropylcellulose, hypromellose, polyvinyl alcohol, xanthan gum, guar gum or polyethylene oxide, more preferably polyethylene oxide.

When the component that exhibits viscosity after dispersion in an aqueous solution is polyethylene oxide, its molecular weight is 100,000 or higher and 10,000,000 or lower, preferably 300,000 or higher and 7,000,000 or lower, more preferably 1,000,000 or higher and 4,000,000 or lower.

When the component that exhibits viscosity after dispersion in an aqueous solution is polyethylene oxide, its content is 30 mg or larger and 500 mg or smaller, preferably 40 mg or larger and 400 mg or smaller, more preferably 50 mg or larger and 300 mg or smaller, per formulation.

By virtue of the "component that exhibits viscosity after dispersion in an aqueous solution" contained in the granules (B), the formulation of the present invention has a drug abuse deterrent property by which a solution of the formulation itself or a solution obtained by pulverizing the formulation, adding water or the like thereto and thoroughly mixing the mixture cannot be sufficiently aspirated into a syringe for injection.

The semi-natural water-soluble polymer is a component having an easily water-soluble property by partially chemically modifying a natural polymer. Specifically, the semi-natural water-soluble polymer is sodium carboxymethylcellulose, methylcellulose, hydroxyethylcellulose, hypromellose or hydroxypropylcellulose, preferably sodium carboxymethylcellulose.

The hydrophobic additive that promotes the disintegration of tablets is a substance that has a property of being poorly dissolved immediately after contact with water. Specific examples thereof can include ethylcellulose, hydrophobic silica, wax and magnesium stearate.

By virtue of the "component that disintegrates the formulation", it is preferred that the formulation of the present invention should disintegrate preferably within 60 minutes, more preferably within 45 minutes.

In the abuse deterrent formulation of the present invention, the granules (A) are contained at a ratio of 90% or less, preferably 80% or less, more preferably 70% or less, of the principal components.

Also, the granules (B) are contained at a ratio of 5% or more, preferably 8% or more, more preferably 15% or more, of the principal components.

Also, the granules (C) are contained at a ratio of 3% or more, preferably 5% or more, more preferably 7% or more, of the principal components.

The principal components are components of the formulation of the present invention, the granules (A), the granules (B), the granules (C) and the like. As for a formulation combined with an additional pharmacologically active substance medically useful for combination, the principal components are the components except for the additional pharmacologically active substance. In the case of a multilayer tablet composed of multiple layers, the principal components are the components except for the additional pharmacologically active substance in layers containing the granules (A), the granules (B) and the granules (C) of the present invention.

The disintegrant is an additive that is generally used in pharmaceutical products to promote disintegration. Specific examples thereof can include, but are not particularly limited to: cellulose derivatives such as low-substituted hydroxypropylcellulose, carboxymethylcellulose, calcium carboxymethylcellulose and internally cross-linked sodium carboxymethylcellulose; cross-linked polyvinylpyrrolidone; and chemically modified starches or celluloses such as carboxymethyl starch and sodium carboxymethyl starch. The disintegrant is preferably low-substituted hydroxypropylcellulose, carboxymethylcellulose, calcium carboxymethylcellulose, internally cross-linked sodium carboxymethylcellulose, sodium carboxymethyl starch or cross-linked polyvinylpyrrolidone, more preferably low-substituted hydroxypropylcellulose.

The polymer that exhibits viscosity when dissolved in an organic solvent is a substance that dissolves in an organic solvent, for example, methanol, ethanol, isopropanol or acetone to exhibit a higher viscosity than before the dissolution. The substance having such a property is not particularly limited. The polymer that exhibits viscosity when dissolved in an organic solvent is preferably hydroxypropylcellulose.

When the polymer that exhibits viscosity when dissolved in an organic solvent is hydroxypropylcellulose, its content is 2 mg or larger and 300 mg or smaller, preferably 10 mg or larger and 200 mg or smaller, more preferably 15 mg or larger and 100 mg or smaller, per formulation.

The manufacturing method for obtaining the abuse deterrent formulation is not particularly limited, and the abuse deterrent formulation can be produced by use of a general method described in the Japanese Pharmacopoeia or a publication such as The Theory and Practice of Industrial Pharmacy (Third Edition) (Leon Lachman et al.: LEA & FEBIGER 1986) or Pharmaceutical Dosage Forms: Tablets volume 1 (Second Edition) (Herbert A. Lieberman et al.: MARCEL DEKKER INC. 1989) without particular limitation. In the manufacturing the granules (B), the non-heating process is a process that prevents the thermal decomposition of the polymer used and does not apply heat at a temperature equal to or higher than the softening point of the polymer. The non-heating process is preferably a dry granulation method.

Examples of the "pharmacologically active drug" used in the abuse deterrent formulation of the present invention can include, but are not particularly limited to, pharmacologically active substances that might not be properly used (might be abused).

For example, the FDA discloses a list of controlled drugs, which is not limited to that described below, and examples of the pharmacologically active drug can also include drugs listed therein:
CFR—Code of Federal Regulations Title 21
PART 1308—SCHEDULES OF CONTROLLED SUBSTANCES Examples of the "pharmacologically active drug" used in the abuse deterrent formulation of the present invention can include narcotic analgesics, opioid analgesics, psychotropics and pharmacologically acceptable salts thereof.

Specific examples thereof can include: acetyl-α-methylfentanyl, acetylmethadol, allylprodine, alpha-acetylmethadol, alpha-methadol, alpha-meprodine, benzethidine, beta-acetylmethadol, β-hydroxyfentanyl, β-hydroxy-3-methylfentanyl, beta-meprodine, beta-methadol, beta-prodine, clonitazene, dextromoramide, diampromide, diethylthiambutene, difenoxin, dimenoxadol, dimepheptanol, dimethylthiambutene, dioxaphetyl butyrate, dipipanone, ethylmethylthiambutene, etonitazene, etoxeridine, furethidine, hydroxypethidine, ketobemidone, levomoramide, levophenacylmorphan, 3-methylfentanyl, 3-methylthiofentanyl, morpheridine, 1-methyl-4-phenyl-4-propionoxypiperidine (MPPP), noracymethadol, norlevorphanol, normethadone, norpipanone, para-fluorofentanyl, (1-(2-phenethyl)-4-phenyl-4-acetoxypiperidine (PEPAP), phenadoxone, phenampromide, phenomorphan, phenoperidine, piritramide, proheptazine, propiram, racemoramide, thiofentanyl, tilidine, trimeperidine, acetorphine, acetyldihydrocodeine, benzylmorphine, codeine methylbromide, codeine-N-oxide, cyprenorphine, desomorphine, dihydromorphine, drotebanol, etorphine, heroin, hydromorphinol, methyldesorphine, methyldihydromorphine, morphine methylbromide, morphine methylsulfonate, morphine-N-oxide, myrophine, nicocodeine, nicomorphine, normorphine, pholcodine, thebacon and tramadol;

opium or opium derivatives (codeine, ethylmorphine, etorphine hydrochloride, dihydroetorphine, hydrocodone, hydromorphone, metopon, morphine, granulated opium, opium extracts, opium solutions, oripavine, oxycodone, oxymorphone, powdered opium, raw opium, thebaine and tincture of opium);

opiates: alfentanil, alpha-prodine, anileridine, bezitramide, dextropropoxyphene, carfentanil, dihydrocodeine, diphenoxylate, fentanyl, isomethadone, levo-alpha-acetylmethadol, levomethorphan, levorphanol, metazocine, methadone, pethidine (meperidine), phenazocine, piminodine, racemethorphan, racemorphan, remifentanil, sufentanil and tapentadol;

central nervous system stimulants: amphetamine, methamphetamine, phenmetrazine, methylphenidate and lisdexamfetamine;

depressants: amobarbital, glutethimide, pentobarbital, phencyclidine, secobarbital, chlorhexadol, embutramide, ketamine, lysergic acid, lysergic acid amide, methyprylon, perampanel, sulfondiethylmethane, sulfonethylmethane, sulfonmethane, tiletamine, zolazepam, Terrazole, nalorphine and buprenorphine;

hallucinogenic substances: nabilone;

stimulants: benzphetamine, chlorphentermine, clortermine and phendimetrazine;

narcotic analgesics: difenoxin and dextropropoxyphene; and depressants: alphaxalone, alprazolam, barbital, bromazepam, camazepam, carisoprodol, chloral betaine, chloral hydrate, chlordiazepoxide, clobazam, clonazepam, clorazepate and clotiazepam.

In the list, hydromorphone or a salt thereof, hydrocodone or a salt thereof, oxycodone or a salt thereof or tramadol or a salt thereof are preferred, and hydrocodone or a salt thereof is more preferred.

The abuse deterrent formulation according to the present invention may be combined with an additional pharmacologically active substance medically useful for combination. Particularly, in the case of using opioid, the abuse deterrent formulation may be combined with a substance having analgesic effects and a substance that compensates for an adverse reaction of the principal agent.

Specific examples thereof include: analgesics such as acetaminophen, aspirin and ibuprofen; antiemetics such as promethazine, metoclopramide, domperidone, haloperidol, prochlorperazine, diphenhydramine, diprophylline, chlorpheniramine maleate and hydroxyzine; and laxatives such as magnesium oxide, magnesium hydroxide, magnesium citrate, lactulose, senna and sodium picosulfate.

In the present invention, a substance that is irritant to the nose when an abuser pulverizes the formulation and snorting the powder through the nose may be contained in the formulation. Specific examples thereof include capsaicin (component of chili peppers) and surfactants (SLS).

The pharmaceutical composition of the present invention can further contain, if necessary, appropriate pharmacologically acceptable additives such as a filler, a lubricant, a binder, a disintegrant, an emulsifier, a flavoring agent and a diluent.

Examples of the "filler" used can include organic excipients including: sugar derivatives such as lactose, saccharose, glucose, mannitol and sorbitol; starch derivatives such as corn starch, potato starch, pregelatinized starch and dextrin; cellulose derivatives such as microcrystalline cellulose; gum arabic; dextran; and pullulan, and inorganic excipients including: silicate derivatives such as light anhydrous silicic acid, synthetic aluminum silicate, calcium silicate and magnesium aluminometasilicate; phosphates such as calcium hydrogen phosphate; carbonates such as calcium carbonate; and sulfates such as calcium sulfate.

Examples of the "lubricant" used can include: stearic acid; stearic acid metal salts such as calcium stearate and magnesium stearate; talc; colloidal silica; waxes such as bees wax and spermaceti; boric acid; adipic acid; sulfates such as sodium sulfate; glycol; fumaric acid; sodium stearyl fumarate; sodium benzoate; D,L-leucine; lauryl sulfates such as sodium lauryl sulfate and magnesium lauryl sulfate; silicic acids such as silicic anhydride and silicic acid hydrate; and the starch derivatives described above.

Examples of the "binder" used can include hydroxypropylcellulose, hypromellose, polyvinylpyrrolidone, macrogol, and the same or similar compounds as those listed as the excipient.

Examples of the "emulsifier" used can include: colloidal clays such as bentonite and veegum; metal hydroxides such as magnesium hydroxide and aluminum hydroxide; anionic surfactants such as sodium lauryl sulfate and calcium stearate; cationic surfactants such as benzalkonium chloride; and nonionic surfactants such as polyoxyethylene alkyl ether, polyoxyethylene sorbitan fatty acid ester and sucrose fatty acid ester.

Examples of the "flavoring agent" used can include: sweeteners such as sodium saccharin and aspartame; acidulants such as citric acid, malic acid and tartaric acid; and flavors such as menthol, lemon and orange.

Examples of the "diluent" used can include lactose, mannitol, glucose, sucrose, calcium sulfate, calcium phosphate, hydroxypropylcellulose, microcrystalline cellulose, water, ethanol, polyethylene glycol, propylene glycol, glycerol, starch, polyvinylpyrrolidone, magnesium aluminometasilicate and mixtures thereof.

The pharmaceutical composition according to the present invention is preferably in a solid dosage form. Examples thereof can include tablets (including sublingual tablets and orally disintegrating tablets), capsules (including soft capsules and microcapsules), granules, fine granules, powders, pills, chewable agents and troches. The solid dosage form is preferably a powder, fine granules, granules, a capsule or a tablet, more preferably a tablet, further preferably a tablet uniformly containing the components and the granules.

In the case of the tablet of the present invention, for example, the tablet is obtained according to a method known per se in the art by granulating the pharmacologically active substance together with a filler, a binder, a disintegrant and the like, followed by drying, screening, addition of a lubricant and the like, mixing and tableting. In this context, the granulation can be performed by any of wet granulation, dry granulation and melt granulation methods and is specifically performed using a high-shear granulator, a fluidized bed granulator, an extrusion granulator, a roller compacter or the like. After the granulation, procedures such as drying and screening may be performed. The tablet or the granules of the present invention may be provided with at least one layer of film coating.

The coating is performed using, for example, a coating machine. Examples of the film coating base include sugar coating bases, water-soluble film coating bases, enteric film coating bases and extended-release film coating bases.

Saccharose is used as a sugar coating base and can be further used in combination with one or two or more members selected from talc, precipitated calcium carbonate, calcium phosphate, calcium sulfate, gelatin, gum arabic, polyvinylpyrrolidone, pullulan and the like.

Examples of the water-soluble film coating base include: cellulose derivatives such as hydroxypropylcellulose, hypromellose, hydroxyethylcellulose, methylhydroxyethylcellulose and sodium carboxymethylcellulose; synthetic polymers such as polyvinyl acetal diethylaminoacetate, aminoalkyl methacrylate copolymers, polyvinylpyrrolidone, polyvinyl alcohol and polyvinyl alcohol copolymers; and polysaccharides such as pullulan.

Examples of the enteric film coating base include: cellulose derivatives such as hypromellose phthalate, hypromellose acetate succinate, carboxymethylethylcellulose and cellulose acetate phthalate; acrylic acid derivatives such as methacrylic acid copolymer L, methacrylic acid copolymer LD and methacrylic acid copolymer S; and natural products such as shellac.

Two or more of these coating bases may be mixed at an appropriate ratio and used. If necessary, appropriate pharmacologically acceptable additives such as a plasticizer, an excipient, a lubricant, a masking agent, a colorant, an antiseptic, an acid and an alkali can be further contained therein.

Hereinafter, the present invention will be described in more detail with reference to Examples, etc. However, the present invention is not intended to be limited by these examples.

EXAMPLES (Example 1) Strength of Granules A

Formulation Examples 1 and 2

Oxycodone hydrochloride trihydrate (Daiichi Sankyo Co., Ltd.), hypromellose acetate succinate (AQOAT AS-LF AS-HF, Shin-Etsu Chemical Co., Ltd.), sodium carboxymethylcellulose (SUNROSE F1400MC, Nippon Paper Chemicals Co., Ltd.) or hypromellose (METOLOSE 90SH-100000SR, Shin-Etsu Chemical Co., Ltd.) and talc (Matsumura Sangyo Co., Ltd.) were mixed in a high-shear granulator (High-Speed Mixer, LFS-GS-1). Triethyl citrate (CITROFLEX, Matsumura Shoji Co., Ltd.) and sodium carboxymethylcellulose (SUNROSE F1400MC, Nippon Paper Chemicals Co., Ltd.) were dissolved in purified water. Then, the solution was added to the mixture and kneaded therewith, and the resultant was loaded to an extrusion granulator (DOMEGRAN DG-L1, Fuji Paudal Co., Ltd.) and extruded. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.) to obtain granules A.

Comparative Example 1

Hypromellose acetate succinate (AQOAT AS-LF, Shin-Etsu Chemical Co., Ltd.), hypromellose (METOLOSE 90SH-100000SR, Shin-Etsu Chemical Co., Ltd.) and talc (Matsumura Sangyo Co., Ltd.) were mixed in a high-shear granulator (High-Speed Mixer, LFS-GS-1). Triethyl citrate (CITROFLEX, Matsumura Shoji Co., Ltd.) was dissolved in purified water. Then, the solution was added to the mixture and kneaded therewith, and the resultant was loaded to an extrusion granulator (DOMEGRAN DG-L1, Fuji Paudal Co., Ltd., screen: 0.6 mm) and extruded. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.) to obtain granules A.

Comparative Example 2

Polyethylene oxide (POLYOX WSR N60K, The Dow Chemical Company), ethylcellulose (ETHOCEL STD100FP, The Dow Chemical Company) and sodium stearyl fumarate (PRUV, JRS Pharma) were mixed in a V-blender, then sieved and compressed in a tableting machine, followed by screening using a cutting mill (Power Mill, Dalton Co., Ltd., screen: φ2 mm) to obtain granules.

(Test Method)

The granules of each example were pulverized in a tablet pulverizer (WONDER CRUSHER WC-3), and the particle size distribution was measured before and after the pulverization. The pulverization conditions were as follows: Pulverization time: 1 minute, sample: 5 g, dial: LEVEL 8

(Results)

As shown in Table 4, in Comparative Example 1, the particle size was evidently decreased after the pulverization. In Comparative Example 2, the particle size of the granules was decreased after the pulverization as compared with before the pulverization, and the strength was found to be weak. On the other hand, in Formulation Examples 1 and 2 containing triethyl citrate, the particle size of the granules did not much change between before and after the pulverization, demonstrating that the granules had large mechanical strength.

TABLE 1

| Components | Formulation Example 1 (mg) |
|---|---|
| Sodium carboxymethylcellulose | 0.65 |
| Triethyl citrate | 10 |
| Purified water | 130.3 |
| Binder solution | 140.95 |
| Oxycodone hydrochloride trihydrate | 5.77 |
| Sodium carboxymethylcellulose | 22.93 |
| Hypromellose acetate succinate LF | 70 |
| Purified water | q.s. |
| Granules A | 109.35 |

TABLE 2

| Components | Formulation Example 2 (mg) | Comparative Example 1 (mg) |
|---|---|---|
| Triethyl citrate | 20 | — |
| Purified water | 110 | — |
| Binder | 130 | — |
| Oxycodone hydrochloride trihydrate | 5.77 | 5.77 |
| METOLOSE 90SH-100000SR | 2 | 2 |
| Hypromellose acetate succinate LF | 70 | 70 |
| Hypromellose acetate succinate HF | 70 | 70 |
| Talc | 20 | 20 |
| Purified water | q.s. | q.s. |
| Granules A | 187.77 | 167.77 |

TABLE 3

| Components | Comparative Example 2 (mg) |
|---|---|
| Polyethylene oxide | 180 |
| Ethylcellulose | 28 |
| Sodium stearyl fumarate | 2 |
| Granules | 210 |

TABLE 4

| Sieve opening (μm) | Formulation Example 1 | | Formulation Example 2 | | Comparative Example 1 | | Comparative Example 2 | |
|---|---|---|---|---|---|---|---|---|
| | % before pulverization | % after pulverization | % before pulverization | % after pulverization | % before pulverization | % after pulverization | % before pulverization | % after pulverization |
| 1400 | 0 | 0 | 0 | 0 | 0 | 0.2 | 26.9 | 0 |
| 1000 | 0.1 | 0 | 1.1 | 0.2 | 0.6 | 0.8 | 22.8 | 1.5 |
| 850 | 2.1 | 0.2 | 8.6 | 0.0 | 2 | 0.6 | 7 | 2 |
| 600 | 18.2 | 3.8 | 18.6 | 3.0 | 65.7 | 2.6 | 11.6 | 6 |
| 300 | 78.9 | 61.7 | 71.7 | 69.1 | 30.2 | 29.4 | 17.4 | 30.3 |

TABLE 4-continued

| Sieve opening (μm) | Formulation Example 1 | | Formulation Example 2 | | Comparative Example 1 | | Comparative Example 2 | |
|---|---|---|---|---|---|---|---|---|
| | % before pulverization | % after pulverization | % before pulverization | % after pulverization | % before pulverization | % after pulverization | % before pulverization | % after pulverization |
| 150 | 0.8 | 26.4 | 0 | 18.7 | 0.5 | 27.2 | 8.7 | 33.1 |
| 75 | 0 | 5.6 | 0 | 7.8 | 0 | 19.9 | 4.4 | 18.4 |
| −75 | 0 | 2.7 | 0 | 1.2 | 1 | 19.3 | 0 | 8.9 |

(Example 2) Disintegration of Tablet

Formulation Example 3 and Comparative Example 3

(Granules A)

Hypromellose acetate succinate (AQOAT AS-LF, Shin-Etsu Chemical Co., Ltd.) and sodium carboxymethylcellulose (SUNROSE F1400MC, Nippon Paper Chemicals Co., Ltd.) were mixed in a high-shear granulator (High-Speed Mixer, LFS-GS-1, Fukae Powtec Corp.). Triethyl citrate (CITROFLEX, Matsumura Shoji Co., Ltd.) was dissolved in purified water. Then, the solution was added to the mixture and kneaded therewith, and the resultant was loaded to an extrusion granulator (DOMEGRAN DG-L1, Fuji Paudal Co., Ltd.) and extruded. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.) to obtain granules A.

(Granules B)

Polyethylene oxide (POLYOX WSRN60K, The Dow Chemical Company), ethylcellulose (ETHOCEL STD100FP, The Dow Chemical Company) and sodium stearyl fumarate (PRUV, JRS Pharma) were mixed, compressed in a tableting machine and then screened by cutting mill (Power Mill, Dalton Co., Ltd., screen: 2 mm) to obtain granules B. In Comparative Example 3, ethylcellulose was not used.

(Granules C)

Microcrystalline cellulose (CEOLUS PH101, Asahi Kasei Chemicals Corp.), KOLLIDON CL (BASF SE) and D-mannitol (Merck KGaA) were mixed. Hydroxypropylcellulose (HPC-L, Nippon Soda Co., Ltd.) was dissolved in purified water. Then, the solution was added to the mixture and kneaded therewith in a high-shear granulator (High-Speed Mixer, LFS-GS-1, Fukae Powtec Corp.), and the resultant was loaded to an extrusion granulator (DOMEGRAN DG-L1, Fuji Paudal Co., Ltd., screen: 0.5 mm) and extruded. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.) to obtain granules C.

(Tablet)

Granules A, granules B, granules C and sodium stearyl fumarate (PRUV, JRS Pharma) were mixed, and the mixed powder was compressed to obtain tablets.

(Test Method)

The disintegration behavior of each formulation was confirmed using a dissolution tester under the conditions given below. The disintegration time of the formulation in a vessel was measured.

[Test Conditions]
Test method: paddle method for dissolution test
Test medium: water, 500 mL
Test medium temperature: 37.0° C.±0.5° C.
Paddle rotation speed: 50 rpm (Results)

As shown in Table 6, the tablet disintegrated rapidly in Formulation Example 3 using granules B supplemented with ethylcellulose as compared with Comparative Example 3 using no ethylcellulose.

TABLE 5

| Components | Formulation Example 3 (mg/tablet) | Comparative Example 3 (mg/tablet) |
|---|---|---|
| Sodium carboxymethylcellulose | 23.58 | 23.58 |
| Hypromellose acetate succinate | 70 | 70 |
| Triethyl citrate | 10 | 10 |
| Granules A | 103.58 | 103.58 |
| Polyethylene oxide | 180 | 180 |
| Ethylcellulose STD100FP | 28 | — |
| Sodium stearyl fumarate | 2 | 2 |
| Granules B | 210 | 182 |
| Microcrystalline cellulose PH101 | 68.6 | 68.6 |
| KOLLIDON CL | 114.3 | 114.3 |
| D-Mannitol | 45.7 | 45.7 |
| Hydroxypropylcellulose | 11.4 | 11.4 |
| Granules C | 240 | 240 |
| Sodium stearyl fumarate | 10 | 10 |
| Total amount | 563.58 | 535.58 |

TABLE 6

| | Formulation Example 3 | Comparative Example 3 |
|---|---|---|
| Disintegration time (min) in dissolution tester | 7 | 15 |

(Example 3) Syringeability Evaluation and Extractability Evaluation in Aqueous Solvent Formulation Examples 4 to 6

(Granules A)

Oxycodone hydrochloride trihydrate (Daiichi Sankyo Co., Ltd.), hypromellose acetate succinate (AQOAT AS-LF, AS-HF, Shin-Etsu Chemical Co., Ltd.), hypromellose (METOLOSE 90SH-100000SR, Shin-Etsu Chemical Co., Ltd.) and talc (Matsumura Sangyo Co., Ltd.) were mixed in a high-shear granulator (High-Speed Mixer, LFS-GS-1, Fukae Powtec Corp.). Triethyl citrate (CITROFLEX, Matsumura Shoji Co., Ltd.) was dissolved in purified water. Then, the solution was added to the mixture and kneaded therewith, and the resultant was loaded to an extrusion granulator (DOMEGRAN DG-L1, Fuji Paudal Co., Ltd., screen: 0.6 mm) and extruded. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.) to obtain granules A.

(Granules B)

Polyethylene oxide (POLYOX WSRN60K, The Dow Chemical Company), ethylcellulose (ETHOCEL STD100FP, The Dow Chemical Company) and sodium stearyl fumarate (PRUV, JRS Pharma) were mixed, compressed in a tableting machine and then screened in a cutting mill (Power Mill, Dalton Co., Ltd., screen: φ2 mm) to obtain granules B.

(Granules C)

Microcrystalline cellulose (CEOLUS PH102, Asahi Kasei Chemicals Corp.), low-substituted hydroxypropylcellulose (L-HPC NBD-022, Shin-Etsu Chemical Co., Ltd.), hydroxypropylcellulose (HPC-SL, Nippon Soda Co., Ltd.) and sodium stearyl fumarate (PRUV, JRS Pharma) were mixed, compressed in a tableting machine and then screened in a cutting mill (Power Mill, Dalton Co., Ltd., screen: φ2 mm) to obtain granules C.

(Tablet)

Granules A, granules B, granules C, microcrystalline cellulose (CEOLUS KG802, Asahi Kasei Chemicals Corp.), hydroxypropylcellulose (HPC-H fine powder, Nippon Soda Co., Ltd.) and sodium stearyl fumarate (PRUV, JRS Pharma) were mixed, and the mixed powder was compressed to obtain tablets.

Formulation Examples 7 to 9

(Granules A)

Oxycodone hydrochloride trihydrate (Daiichi Sankyo Co., Ltd.), hypromellose acetate succinate (AQOAT AS-LF, Shin-Etsu Chemical Co., Ltd.) and sodium carboxymethylcellulose (SUNROSE F1400MC, Nippon Paper Chemicals Co., Ltd.) were mixed in a high-shear granulator (High-Speed Mixer, LFS-GS-1, Fukae Powtec Corp.). Triethyl citrate (CITROFLEX, Matsumura Shoji Co., Ltd.) or triacetin (Kanto Chemical Co., Inc.) was dissolved in purified water. Then, the solution was added to the mixture and kneaded therewith, and the resultant was loaded to an extrusion granulator (DOMEGRAN DG-L1, Fuji Paudal Co., Ltd., screen: 0.6 mm) and extruded. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.) to obtain granules A.

(Granules B)

Polyethylene oxide (POLYOX WSRN60K, The Dow Chemical Company), ethylcellulose (ETHOCEL STD100FP, The Dow Chemical Company) and sodium stearyl fumarate (PRUV, JRS Pharma) were mixed, compressed in a tableting machine and then screened in a cutting mill (Power Mill, Dalton Co., Ltd., screen: φ2 mm) to obtain granules B.

(Granules C)

Microcrystalline cellulose (CEOLUS PH102, Asahi Kasei Chemicals Corp.), low-substituted hydroxypropylcellulose (L-HPC NBD-022, Shin-Etsu Chemical Co., Ltd.), hydroxypropylcellulose (HPC-SL, Nippon Soda Co., Ltd.) and sodium stearyl fumarate (PRUV, JRS Pharma) were mixed, compressed in a tableting machine and then screened in a cutting mill (Power Mill, Dalton Co., Ltd., screen: φ2 mm) to obtain granules C.

(Tablet)

Granules A, granules B, granules C, microcrystalline cellulose (CEOLUS PH802, Asahi Kasei Chemicals Corp.), hydroxypropylcellulose (HPC-H fine powder, Nippon Soda Co., Ltd.) and sodium stearyl fumarate (PRUV, JRS Pharma) were mixed, and the mixed powder was compressed to obtain tablets.

Formulation Examples 10 and 11

(Granules A)

Tramadol hydrochloride (PROTOCHEMICALS AG), hypromellose acetate succinate (AQOAT AS-LF, AS-HF, Shin-Etsu Chemical Co., Ltd.), hypromellose (METOLOSE 90SH-100000SR, Shin-Etsu Chemical Co., Ltd.) and low-substituted hydroxypropylcellulose (Shin-Etsu Chemical Co., Ltd., L-HPC NBD-022) were mixed in a high-shear granulator (High-Speed Mixer, LFS-GS-1, Fukae Powtec Corp.). Triethyl citrate (CITROFLEX, Matsumura Shoji Co., Ltd.) was dissolved in purified water. Then, the solution was added to the mixture and kneaded therewith, and the resultant was loaded to an extrusion granulator (DOMEGRAN DG-L1, Fuji Paudal Co., Ltd., screen: 0.6 mm) and extrusion-granulated. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.) to obtain granules A.

(Granules B)

Polyethylene oxide (POLYOX WSRN60K, The Dow Chemical Company), ethylcellulose (ETHOCEL STD100FP, The Dow Chemical Company) and sodium stearyl fumarate (PRUV, JRS Pharma) were mixed, compressed in a tableting machine and then screened in a cutting mill (Power Mill, Dalton Co., Ltd., screen: φ2 mm) to obtain granules B.

(Granules C)

Microcrystalline cellulose (CEOLUS PH102, Asahi Kasei Chemicals Corp.), low-substituted hydroxypropylcellulose (L-HPC NBD-022, Shin-Etsu Chemical Co., Ltd.), hydroxypropylcellulose (HPC-SL, Nippon Soda Co., Ltd.) and sodium stearyl fumarate (PRUV, JRS Pharma) were mixed, compressed in a tableting machine and then screened in a cutting mill (Power Mill, Dalton Co., Ltd., screen: φ2 mm) to obtain granules C.

(Tablet)

Granules A, granules B, granules C, microcrystalline cellulose (CEOLUS KG802, Asahi Kasei Chemicals Corp.), hydroxypropylcellulose (HPC-H fine powder, Nippon Soda Co., Ltd.) and sodium stearyl fumarate (PRUV, JRS Pharma) were mixed, and the mixed powder was compressed to obtain tablets.

Formulation Example 12

(Granules A)

Tramadol hydrochloride (PROTOCHEMICALS AG), hypromellose acetate succinate (AQOAT AS-LF, Shin-Etsu Chemical Co., Ltd.) and sodium carboxymethylcellulose (SUNROSE F1400MC, Nippon Paper Chemicals Co., Ltd.)) were mixed in a high-shear granulator (High-Speed Mixer, LFS-GS-1, Fukae Powtec Corp.). Triethyl citrate (CITROFLEX, Matsumura Shoji Co., Ltd.) was dissolved in purified water. Then, the solution was added to the mixture and kneaded therewith, and the resultant was loaded to an extrusion granulator (DOMEGRAN DG-L1, Fuji Paudal Co., Ltd., screen: 0.6 mm) and extruded. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.) to obtain granules A.

(Granules B)

Polyethylene oxide (POLYOX WSRN60K, The Dow Chemical Company), ethylcellulose (ETHOCEL STD100FP, The Dow Chemical Company) and sodium stearyl fumarate (PRUV, JRS Pharma) were mixed, compressed in a tableting machine and then screened in a cutting mill (Power Mill, Dalton Co., Ltd., screen: φ2 mm) to obtain granules B.

(Granules C)

Microcrystalline cellulose (CEOLUS PH102, Asahi Kasei Chemicals Corp.), low-substituted hydroxypropylcellulose (L-HPC NBD-022, Shin-Etsu Chemical Co., Ltd.), hydroxypropylcellulose (HPC-SL, Nippon Soda Co., Ltd.) and sodium stearyl fumarate (PRUV, JRS Pharma) were mixed, compressed in a tableting machine and then screened in a cutting mill (Power Mill, Dalton Co., Ltd., screen: φ2 mm) to obtain granules C.

(Tablet)

Granules A, granules B, granules C, microcrystalline cellulose (CEOLUS KG802, Asahi Kasei Chemicals Corp.) and sodium stearyl fumarate (JRS Pharma, PRUV) were mixed, and the mixed powder was compressed to obtain tablets.

Evaluation of Syringeability

Solution for use in syringeability evaluation (evaluation solution): water

Amount of the solution for use in syringeability evaluation: 10 mL

Syringeability evaluation operation: 10 mL of water is added to a pulverized tablet and thoroughly mixed therewith. The mixture is collected using a syringe (10 mL) equipped with an injection needle (27 G). The syringeability is evaluated according to the amount that can be collected for 1 minute.

(Test): Evaluation of Drug Extractability from Formulation Containing Oxycodone Hydrochloride 10 mL of a solution for extraction is added with respect to one tablet, and the extract is collected into a syringe via cotton. The amount of the drug (oxycodone hydrochloride trihydrate or tramadol hydrochloride) in the collected extract is determined to evaluate the extraction resistance of the formulation. A smaller amount of the drug in the extract means being less extractable. Namely, the formulation is evaluated as having high extraction resistance.

[Extraction Test Conditions]

Solution for extraction: saline

Amount of the solution for use in extraction: 10 mL

Extraction operation: A tablet or a broken tablet is placed in a glass beaker, to which 10 mL of the solution for extraction is then added. The beaker is left standing for a predetermined period of time, and then, the mixture of the tablet and the solution is stirred using a spatula. Absorbent cotton is placed in the mixture thus stirred, and the extract is collected via the absorbent cotton using a syringe (10 mL) equipped with an injection needle (18 G).

The concentration of the drug in the extract collected by the extraction operation is determined. The amount of the drug extracted from the tablet is calculated using the obtained quantification value to determine the rate of extraction (ratio of the amount of the drug extracted to the amount of the drug contained in one tablet).

The quantification is carried out using high-performance liquid chromatography (HPLC) or an ultraviolet absorptiometer under the following conditions.

Quantification of Oxycodone Hydrochloride Trihydrate

[Measurement Conditions for High-Performance Liquid Chromatography]

Analytical column: Shim-pack XR-ODS (3.0 mm I.D.×50 mm, particle size: 2.2 μm, Shimadzu Corp.)

Mobile phase A: 0.015 mol/L sodium 1-heptane sulfonate solution (pH 2.5)

Mobile phase B: methanol

Solution sending conditions:

| Time (min) | Mobile phase A (Vol %) | Mobile phase B (Vol %) |
|---|---|---|
| 0 to 10 | 74 | 26 |

Flow rate: approximately 0.5 mL per minute

Column temperature: 50° C.

Injection volume: 5 μL

Detector: ultraviolet absorptiometer (measurement wavelength: 230 nm)

Quantification of Tramadol Hydrochloride

[Measurement Conditions for Ultraviolet Absorptiometry] Measurement Wavelength: 273 nm

[Measurement Conditions for High-Performance Liquid Chromatography]

Test Conditions (HPLC)

Detector: ultraviolet absorptiometer (measurement wavelength: 273 nm)

Analytical column: Symmetry C8, Waters (3.9 mmφ×150 mm, 5 μm), Waters Corp.

Mobile phase: Solution A/acetonitrile (770/230)

In this context, Solution A is a solution prepared by adding 28% ammonia water to a mixed solution of 991.5 mL of water and 5 mL of perchloric acid and adjusting the pH to 2.2±0.2.

Flow rate: approximately 2.0 mL per minute

Column temperature: room temperature

Injection volume: 20 μL

Detector: ultraviolet absorptiometer (measurement wavelength: 273 nm)

(Results)

As shown in Tables 9, 10, 13 and 14, in all of the formulation examples, the solution was unable to be obtained via a syringe because polyethylene oxide was used. In addition, in all of the formulation examples, the drug was hardly extracted from the formulation into saline.

TABLE 7

| Components | Formulation Example 4 (mg/tablet) | Formulation Example 5 (mg/tablet) | Formulation Example 6 (mg/tablet) |
|---|---|---|---|
| Triethyl citrate | 20 | 20 | 20 |
| Purified water | 110 | 110 | 110 |
| Binder | 130 | 130 | 130 |
| Oxycodone hydrochloride trihydrate | 5.77 | 5.77 | 5.77 |
| METOLOSE 90SH-100000SR | 2 | 2 | 2 |
| Hypromellose acetate succinate LF | 70 | 70 | 70 |
| Hypromellose acetate succinate HF | 70 | 70 | 70 |
| Talc | 20 | 20 | 20 |
| Purified water | q.s. | q.s. | q.s. |
| Granules A | 187.77 | 187.77 | 187.77 |
| Polyethylene oxide | 180 | 180 | 180 |
| Ethylcellulose STD 100 FP | 28 | 28 | 28 |
| Sodium stearyl fumarate | 2 | 2 | 2 |
| Granules B | 210 | 210 | 210 |
| Microcrystalline cellulose PH102 | 35.36 | 35 | 35 |
| Low-substituted hydroxypropylcellulose | 106.07 | 155 | 155 |

TABLE 7-continued

| Components | Formulation Example 4 (mg/tablet) | Formulation Example 5 (mg/tablet) | Formulation Example 6 (mg/tablet) |
|---|---|---|---|
| Hydroxypropylcellulose | 7.07 | 8 | 0 |
| Sodium stearyl fumarate | 1.5 | 2 | 2 |
| Granules C | 150 | 200 | 192 |
| Hydroxypropylcellulose HPC-H | 50 | 25 | 25 |
| Microcrystalline cellulose KG802 | 50 | 50 | 50 |
| Sodium stearyl fumarate | 10 | 10 | 10 |
| Total amount | 657.77 | 682.77 | 674.77 |

TABLE 8

| Components | Formulation Example 7 (mg/tablet) | Formulation Example 8 (mg/tablet) | Formulation Example 9 (mg/tablet) |
|---|---|---|---|
| Triethyl citrate | 10 | 10 | — |
| Triacetin | — | — | 14.4 |
| Purified water | 130.3 | 130.3 | 189.6 |
| Binder | 140.3 | 140.3 | 204 |
| Oxycodone hydrochloride trihydrate | 5.77 | 5.77 | 5.77 |
| Sodium carboxymethylcellulose | 23.58 | 23.58 | 23.58 |
| Hypromellose acetate succinate LF | 70 | 70 | 210 |
| Purified water | q.s. | q.s. | q.s. |
| Granules A | 109.35 | 109.35 | 253.95 |
| Polyethylene oxide | 180 | 180 | 180 |
| Ethylcellulose STD 100 FP | 28 | 28 | 28 |
| Sodium stearyl fumarate | 2 | 2 | 2 |
| Granules B | 210 | 210 | 210 |
| Microcrystalline cellulose PH 102 | 174.43 | 35.36 | 35.36 |
| Low-substituted hydroxypropylcellulose | 174.43 | 106.07 | 106.07 |
| Hydroxypropylcellulose | 17.44 | 7.07 | 7.07 |
| Sodium stearyl fumarate | 3.7 | 1.5 | 1.5 |
| Granules C | 370 | 150 | 150 |
| Hydroxypropylcellulose HPC-H | — | 50 | — |
| Microcrystalline cellulose KG802 | — | 50 | 50 |
| Sodium stearyl fumarate | 10 | 10 | 10 |
| Total amount | 699.35 | 579.35 | 673.95 |

(Syringeability)

TABLE 9

| Formulation | Formulation Example 4 | Formulation Example 5 | Formulation Example 6 | Formulation Example 7 | Formulation Example 8 | Formulation Example 9 |
|---|---|---|---|---|---|---|
| Amount of solution via syringe (mL) | 0 | 0 | 0 | 0 | 0 | 0 |

(Rate of Extraction)

TABLE 10

| Formulation | Formulation Example 4 | Formulation Example 5 | Formulation Example 6 | Formulation Example 7 | Formulation Example 8 | Formulation Example 9 |
|---|---|---|---|---|---|---|
| Rate of drug extraction (%) | 0 | 0 | 0 | 0 | 2 | 0 |

TABLE 11

| Components | Formulation Example 10 (mg/tablet) | Formulation Example 11 (mg/tablet) |
|---|---|---|
| Triethyl citrate | 40 | 40 |
| Purified water | 220 | 220 |
| Binder | 260 | 260 |
| Tramadol hydrochloride | 50 | 50 |
| METOLOSE 90SH-100000SR | 4 | 4 |
| Hypromellose acetate succinate LF | 140 | 140 |
| Hypromellose acetate succinate HF | 140 | 140 |
| Low-substituted hydroxypropylcellulose | 80 | 80 |
| Purified water | q.s. | q.s. |
| Granules A | 454 | 454 |
| Polyethylene oxide | 180 | 180 |
| Ethylcellulose STD 100 FP | 28 | 28 |
| Sodium stearyl fumarate | 2 | 2 |
| Granules B | 210 | 210 |
| Microcrystalline cellulose PH102 | 35.36 | 35.36 |
| Low-substituted hydroxypropylcellulose | 106.07 | 106.07 |
| Hydroxypropylcellulose | 7.07 | 7.07 |
| Sodium stearyl fumarate | 1.5 | 1.5 |
| Granules C | 150 | 150 |
| Hydroxypropylcellulose HPC-H | — | 50 |
| Microcrystalline cellulose KG802 | 50 | 50 |
| Sodium stearyl fumarate | 10 | 10 |
| Total amount | 874 | 924 |

TABLE 12

| Components | Formulation Example 12 (mg/tablet) |
|---|---|
| Triethyl citrate | 30 |
| Purified water | 165 |
| Binder | 195 |
| Tramadol hydrochloride | 50 |
| Sodium carboxymethylcellulose | 50 |
| Hypromellose acetate succinate LF | 105 |
| Hypromellose acetate succinate HF | 105 |
| Purified water | q.s. |
| Granules A | 340 |
| Polyethylene oxide | 180 |
| Ethylcellulose STD 100 FP | 28 |
| Sodium stearyl fumarate | 2 |
| Granules B | 210 |
| Microcrystalline cellulose PH102 | 35.36 |
| Low-substituted hydroxypropylcellulose | 106.07 |
| Hydroxypropylcellulose | 7.07 |
| Sodium stearyl fumarate | 1.5 |
| Granules C | 150 |

TABLE 12-continued

| Components | Formulation Example 12 (mg/tablet) |
|---|---|
| Microcrystalline cellulose KG802 | 50 |
| Sodium stearyl fumarate | 10 |
| Total amount | 810 |

(Syringeability)

TABLE 13

| Formulation | Formulation Example 10 | Formulation Example 11 | Formulation Example 12 |
|---|---|---|---|
| Amount of solution via syringe (mL) | 0 | 0 | 0 |

(Rate of Extraction)

TABLE 14

| Formulation | Formulation Example 10 | Formulation Example 11 | Formulation Example 12 |
|---|---|---|---|
| Drug extraction (%) | 0 | 0 | 0 |

(Example 4) Syringeability Evaluation in Aqueous Solvent

Formulation Example 13

(Granules A)
Oxycodone hydrochloride (Mallinckrodt Pharmaceuticals), hypromellose acetate succinate (AQOAT AS-LF, AS-HF, Shin-Etsu Chemical Co., Ltd.), hypromellose (METOLOSE 90SH-100000SR, Shin-Etsu Chemical Co., Ltd.) and talc (Matsumura Sangyo Co., Ltd.) were mixed in a mortar. Triethyl citrate (CITROFLEX, Matsumura Shoji Co., Ltd.) was dissolved in purified water. Then, the solution was added to the mixture and kneaded therewith, and the resultant was loaded to an extrusion granulator (DOMEGRAN DG-L1, Fuji Paudal Co., Ltd., screen: 0.6 mm) and extruded. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.) to obtain granules A.

(Granules B)
Polyethylene oxide (POLYOX WSRN60K, The Dow Chemical Company), ethylcellulose (ETHOCEL STD100FP, The Dow Chemical Company) and sodium stearyl fumarate (PRUV, JRS Pharma) were mixed, compressed in a tableting machine and then screened in a cutting mill (Power Mill, Dalton Co., Ltd., screen: 10 mm square, φ2 mm) to obtain granules B.

(Granules C)
Microcrystalline cellulose (CEOLUS PH102, Asahi Kasei Chemicals Corp.), low-substituted hydroxypropylcellulose (L-HPC NBD-022, Shin-Etsu Chemical Co., Ltd.), hydroxypropylcellulose (HPC-SL, Nippon Soda Co., Ltd.) and sodium stearyl fumarate (PRUV, JRS Pharma) were mixed, compressed in a tableting machine and then screened in a cutting mill (Power Mill, Dalton Co., Ltd., screen: 10 mm square, φ2 mm) to obtain granules C.

(Tablet)
Granules A, granules B, granules C, microcrystalline cellulose (CEOLUS KG802, Asahi Kasei Chemicals Corp.), hydroxypropylcellulose (HPC-H fine powder, Nippon Soda Co., Ltd.) and sodium stearyl fumarate (PRUV, JRS Pharma) were mixed, and the mixed powder was compressed to obtain tablets.

Formulation Example 14

(Granules A)
Hydrocodone bitartrate (Daiichi Sankyo Co., Ltd.), ethylcellulose (ETHOCEL STD100FP, The Dow Chemical Company), hypromellose acetate succinate (AQOAT AS-LF, AS-HF, Shin-Etsu Chemical Co., Ltd.), hypromellose (METOLOSE 90SH-100000SR, Shin-Etsu Chemical Co., Ltd.) and talc (Matsumura Sangyo Co., Ltd.) were mixed in a mortar. Triethyl citrate (CITROFLEX, Matsumura Shoji Co., Ltd.) was dissolved in purified water. Then, the solution was added to the mixture and kneaded therewith, and the resultant was loaded to an extrusion granulator (DOMEGRAN DG-L1, Fuji Paudal Co., Ltd., screen: 0.6 mm) and extruded. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.) to obtain granules A.

(Granules B)
Polyethylene oxide (POLYOX WSRN60K, The Dow Chemical Company), ethylcellulose (ETHOCEL STD100FP, The Dow Chemical Company) and sodium stearyl fumarate (PRUV, JRS Pharma) were mixed, compressed in a tableting machine and then screened in a cutting mill (Power Mill, Dalton Co., Ltd., screen: 10 mm square, φ2 mm) to obtain granules B.

(Granules C)
Microcrystalline cellulose (CEOLUS PH102, Asahi Kasei Chemicals Corp.), low-substituted hydroxypropylcellulose (L-HPC NBD-022, Shin-Etsu Chemical Co., Ltd.), hydroxypropylcellulose (HPC-SL, Nippon Soda Co., Ltd.) and sodium stearyl fumarate (PRUV, JRS Pharma) were mixed, compressed in a tableting machine and then crushed in a particle size selector (Power Mill, Dalton Co., Ltd., screen: 10 mm square, φ2 mm) to obtain granules C.

(Tablet)
Granules A, granules B, granules C, microcrystalline cellulose (CEOLUS KG802, Asahi Kasei Chemicals Corp.), hydroxypropylcellulose (HPC-H fine powder, Nippon Soda Co., Ltd.), acetaminophen (Compap-L, Mallinckrodt Pharmaceuticals) and sodium stearyl fumarate (PRUV, JRS Pharma) were mixed, and the mixed powder was compressed to obtain tablets.

Evaluation of Syringeability
Solution for use in syringeability evaluation (evaluation solution): water or saline
Amount of the solution for use in syringeability evaluation: 10 mL
Syringeability evaluation operation: 10 mL of water or saline is added to a pulverized tablet and thoroughly mixed therewith. The mixture is collected using a syringe (10 mL) equipped with an injection needle (27 G). The syringeability is evaluated according to the amount that can be collected for 1 minute.

(Results)
As shown in Table 17, in all of the formulation examples, the solution was hardly able to be obtained via a syringe because polyethylene oxide was used.

TABLE 15

| Components | Formulation Example 13 (mg/tablet) |
|---|---|
| Triethyl citrate | 30 |
| Purified water | 165 |
| | |
| Binder | 195 |
| Oxycodone hydrochloride | 5 |
| METOLOSE 90SH-100000SR | 3 |
| Hypromellose acetate succinate LF | 105 |
| Hypromellose acetate succinate HF | 105 |
| Talc | 30 |
| | |
| Purified water | q.s. |
| Granules A | 278 |
| Polyethylene oxide | 140 |
| Ethylcellulose STD 100 FP | 21.78 |
| Sodium stearyl fumarate | 1.56 |
| | |
| Granules B | 163.3 |
| Microcrystalline cellulose PH102 | 47.25 |
| Low-substituted hydroxypropylcellulose | 209.25 |
| Hydroxypropylcellulose | 10.8 |
| Sodium stearyl fumarate | 2.7 |
| | |
| Granules C | 270 |
| Hydroxypropylcellulose HPC-H | 25 |
| Microcrystalline cellulose KG802 | 50 |
| Sodium stearyl fumarate | 10 |
| | |
| Total amount | 796.3 |

TABLE 16

| Components | Formulation Example 14 (mg/tablet) |
|---|---|
| Triethyl citrate | 19 |
| Purified water | 105 |
| | |
| Binder | 124 |
| Hydrocodone bitartrate | 7.5 |
| Ethylcellulose STD 100 FP | 40 |
| METOLOSE 90SH-100000SR | 3 |
| Hypromellose acetate succinate LF | 50 |
| Hypromellose acetate succinate HF | 50 |
| Talc | 30 |
| Purified water | q.s. |
| | |
| Granules A | 199.5 |
| Polyethylene oxide | 140 |
| Ethylcellulose STD 100 FP | 21.78 |
| Sodium stearyl fumarate | 1.56 |
| | |
| Granules B | 163.3 |
| Microrystalline cellulose PH102 | 8.75 |
| Low-substituted hydroxypropylcellulose | 38.75 |
| Hydroxypropylcellulose | 2 |
| Sodium stearyl fumarate | 0.5 |
| | |
| Granules C | 50 |
| Hydroxypropylcellulose HPC-H | 25 |
| Acetaminophen Compap-L | 361.1 |
| Sodium stearyl fumarate | 10 |
| | |
| Total amount | 808.9 |

(Syringeability)

TABLE 17

| Formulation | | Formulation Example 13 | Formulation Example 14 |
|---|---|---|---|
| Amount of solution via syringe (mL) | Saline | 0 | 1 |
| | Water | 0 | 0.6 |

(Example 5) Extractability from Organic Solvent

Formulation Examples 15 to 18

(Granules A)
Oxycodone hydrochloride trihydrate (Daiichi Sankyo Co., Ltd.), hypromellose acetate succinate (AQOAT AS-LF, AS-HF, Shin-Etsu Chemical Co., Ltd.), hypromellose (METOLOSE 90SH-100000SR, Shin-Etsu Chemical Co., Ltd.) and talc (Matsumura Sangyo Co., Ltd.) were mixed in a high-shear granulator (High-Speed Mixer, LFS-GS-1, Fukae Powtec Corp.). Triethyl citrate (CITROFLEX, Matsumura Shoji Co., Ltd.) was dissolved in purified water. Then, the solution was added to the mixture and kneaded therewith, and the resultant was loaded to an extrusion granulator (DOMEGRAN DG-L1, Fuji Paudal Co., Ltd., screen: 0.6 mm) and extruded. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.) to obtain granules A.

(Granules B)
Polyethylene oxide (POLYOX WSRN60K, The Dow Chemical Company), ethylcellulose (ETHOCEL STD100FP, The Dow Chemical Company) and sodium stearyl fumarate (PRUV, JRS Pharma) were mixed, compressed in a tableting machine and then screened in a cutting mill (Power Mill, Dalton Co., Ltd., screen: φ2 mm) to obtain granules B.

(Granules C)
Microcrystalline cellulose (CEOLUS PH102, Asahi Kasei Chemicals Corp.), low-substituted hydroxypropylcellulose (L-HPC NBD-022, Shin-Etsu Chemical Co., Ltd.), hydroxypropylcellulose (HPC-SL, Nippon Soda Co., Ltd.) and sodium stearyl fumarate (PRUV, JRS Pharma) were mixed and screened in a cutting mill (Power Mill, Dalton Co., Ltd., screen: φ2 mm) to obtain granules C.

(Tablet)
Granules A, granules B, granules C, Microcrystalline cellulose (CEOLUS KG802, Asahi Kasei Chemicals Corp.), hydroxypropylcellulose (HPC-H fine powder, Nippon Soda Co., Ltd.) and sodium stearyl fumarate (PRUV, JRS Pharma) were mixed, and the mixed powder was compressed to obtain tablets.

Formulation Examples 19 to 21

(Granules A)
Oxycodone hydrochloride trihydrate (Daiichi Sankyo Co., Ltd.), hypromellose acetate succinate (AQOAT AS-LF, Shin-Etsu Chemical Co., Ltd.) and sodium carboxymethylcellulose (SUNROSE F1400MC, Nippon Paper Chemicals Co., Ltd.)) were mixed in a high-shear granulator (High-Speed Mixer, LFS-GS-1, Fukae Powtec Corp.). Triethyl citrate (CITROFLEX, Matsumura Shoji Co., Ltd.) or triacetin (Kanto Chemical Co., Inc.) was dissolved in purified water. Then, the solution was added to the mixture and kneaded therewith, and the resultant was loaded to an extrusion granulator (DOMEGRAN DG-L1, Fuji Paudal Co., Ltd., screen: 0.6 mm) and extruded. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.) to obtain granules A.

(Granules B)

Polyethylene oxide (POLYOX WSRN60K, The Dow Chemical Company), ethylcellulose (ETHOCEL STD100FP, The Dow Chemical Company) and sodium stearyl fumarate (PRUV, JRS Pharma) were mixed, compressed in a tableting machine and then screened in a cutting mill (Power Mill, Dalton Co., Ltd., screen: φ2 mm) to obtain granules B.

(Granules C)

Microcrystalline cellulose (CEOLUS PH102, Asahi Kasei Chemicals Corp.), low-substituted hydroxypropylcellulose (L-HPC NBD-022, Shin-Etsu Chemical Co., Ltd.), hydroxypropylcellulose (Nippon Soda Co., Ltd., HPC-SL) and sodium stearyl fumarate (PRUV, JRS Pharma) were mixed to obtain granules C.

(Tablet)

Granules A, granules B, granules C, Microcrystalline cellulose (CEOLUS KG802, Asahi Kasei Chemicals Corp.), hydroxypropylcellulose (HPC-H fine powder, Nippon Soda Co., Ltd.) and sodium stearyl fumarate (PRUV, JRS Pharma) were mixed, and the mixed powder was compressed to obtain tablets.

Comparative Example 4

Oxycodone hydrochloride trihydrate (Daiichi Sankyo Co., Ltd.), polyethylene oxide (POLYOX WSR303, The Dow Chemical Company), polyethylene glycol (macrogol 6000, NOF Corp.) and hypromellose (METOLOSE 90SH-100000SR, Shin-Etsu Chemical Co., Ltd.) were mixed in a mortar, and the mixture was loaded to an extruder (HAAK MINICTW, Thermo Fisher Scientific Inc.) and then heated to 120° C. to obtain an extrudate. The extrudate was cut using a cutter to obtain granules.

The formulations of Formulations 10 to 12 of Example 3 were used as formulations containing tramadol hydrochloride.

(Test) Evaluation of Drug Extractability from Formulation 10 mL of a solvent for extraction is added with respect to one tablet, and the extract is collected into a syringe via cotton. The amount of the drug (oxycodone hydrochloride trihydrate or tramadol hydrochloride) in the collected extract is determined to evaluate the extraction resistance of the formulation. A smaller amount of the drug in the extract means being less extractable. Namely, the formulation is evaluated as having high extraction resistance.

[Extraction Test Conditions]

Solvent for extraction: methanol, ethanol, 2-propanol or acetone

Amount of the solvent for use in extraction: 10 mL

Extraction operation: A tablet or a broken tablet is placed in a glass beaker, to which 10 mL of the solvent for extraction is then added. The beaker is left standing for a predetermined period of time, and then, the mixture of the tablet and the solvent is stirred using a spatula. Absorbent cotton is placed in the mixture thus stirred, and the extract is collected via the cotton using a syringe (10 mL) equipped with an injection needle (18 G).

The concentration of the drug in the extract collected by the extraction operation is determined. The amount of the drug extracted from the tablet is calculated using the obtained quantification value to determine the rate of extraction (ratio of the amount of the drug extracted to the amount of the drug contained in one tablet).

The quantification is carried out using high-performance liquid chromatography (HPLC) or an ultraviolet absorptiometer under the following conditions.

The quantification of the drug was carried out under the conditions used in Example 3.

(Results)

As shown in Tables 21 and 22, even in Formulation Example 15 using neither hydroxypropylcellulose (HPC-H) nor sodium carboxymethylcellulose, the extractability of the drug into the organic solvent was low. In Formulation Examples 16 to 21 using either of hydroxypropylcellulose (HPC-H) or sodium carboxymethylcellulose, the extractability of the drug into the organic solvent was found to be lower. Particularly, for methanol, as shown in Table 21, the amount of the drug extracted from the granules produced by the hot melt extrusion method of Comparative Example 4 was high as compared with Formulation Examples 16 to 21.

TABLE 18

| Components | Formulation Example 15 (mg/tablet) | Formulation Example 16 (mg/tablet) | Formulation Example 17 (mg/tablet) | Formulation Example 18 (mg/tablet) |
|---|---|---|---|---|
| Triethyl citrate | 20 | 20 | 20 | 20 |
| Purified water | 110 | 110 | 110 | 110 |
| Binder | 130 | 130 | 130 | 130 |
| Oxycodone hydrochloride trihydrate | 5.77 | 5.77 | 5.77 | 5.77 |
| METOLOSE 90SH-100000SR | 2 | 2 | 2 | 2 |
| Hypromellose acetate succinate LF | 70 | 70 | 70 | 70 |
| Hypromellose acetate succinate HF | 70 | 70 | 70 | 70 |
| Talc | 20 | 20 | 20 | 20 |
| Purified water | q.s. | q.s. | q.s. | q.s. |
| Granules A | 187.77 | 187.77 | 187.77 | 187.77 |
| Polyethylene oxide | 180 | 180 | 180 | 180 |
| Ethylcellulose STD 100 FP | 28 | 28 | 28 | 28 |
| Sodium stearyl fumarate | 2 | 2 | 2 | 2 |
| Granules B | 210 | 210 | 210 | 210 |
| Microcrystalline cellulose PH102 | 35.36 | 35.36 | 35.36 | 35.36 |
| Low-substituted hydroxypropylcellulose | 106.07 | 106.07 | 106.07 | 106.07 |

TABLE 18-continued

| Components | Formulation Example 15 (mg/tablet) | Formulation Example 16 (mg/tablet) | Formulation Example 17 (mg/tablet) | Formulation Example 18 (mg/tablet) |
|---|---|---|---|---|
| Hydroxypropylcellulose | 7.07 | 7.07 | 7.07 | 7.07 |
| Sodium stearyl fumarate | 1.5 | 1.5 | 1.5 | 1.5 |
| Granules C | 150 | 150 | 150 | 150 |
| Hydroxypropylcellulose HPC-H | — | 25 | 50 | 100 |
| Microcrystalline cellulose KG802 | 50 | 50 | 50 | 50 |
| Sodium stearyl fumarate | 10 | 10 | 10 | 10 |
| Total amount | 607.77 | 632.77 | 657.77 | 707.77 |

TABLE 19

| Components | Formulation Example 19 (mg) | Formulation Example 20 (mg) | Formulation Example 21 (mg) |
|---|---|---|---|
| Triethyl citrate | 10 | 10 | — |
| Triacetin | — | — | 14.4 |
| Purified water | 130.3 | 130.3 | 189.6 |
| Binder | 140.3 | 140.3 | 204 |
| Oxycodone hydrochloride trihydrate | 5.77 | 5.77 | 5.77 |
| Sodium carboxymethylcellulose | 23.58 | 23.58 | 23.58 |
| Hypromellose acetate succinate LF | 70 | 70 | 210 |
| Purified water | q.s. | q.s. | q.s. |
| Granules A | 109.35 | 109.35 | 253.95 |
| Polyethylene oxide | 180 | 180 | 180 |
| Ethylcellulose STD 100 FP | 28 | 28 | 28 |
| Sodium stearyl fumarate | 2 | 2 | 2 |
| Granules B | 210 | 210 | 210 |
| Microcrystalline cellulose PH102 | 174.43 | 35.36 | 35.36 |
| Low-substituted hydroxypropylcellulose | 174.43 | 106.07 | 106.07 |
| Hydroxypropylcellulose | 17.44 | 7.07 | 7.07 |
| Sodium stearyl fumarate | 3.7 | 1.5 | 1.5 |
| Granules C | 370 | 150 | 150 |
| Hydroxypropylcellulose HPC-H | — | 50 | — |
| Microcrystalline cellulose KG802 | — | 50 | 50 |
| Sodium stearyl fumarate | 10 | 10 | 10 |
| Total amount | 699.35 | 579.35 | 673.95 |

Comparative Example 4

TABLE 20

| Components | Comparative Example 4 (mg/tablet) |
|---|---|
| Oxycodone hydrochloride trihydrate | 5.77 |
| Polyethylene glycol macrogol 6000 | 14 |
| METOLOSE 90SH-100000SR | 14 |
| Polyethylene oxide | 68 |
| Granules | 101.77 |

(Extractability of Oxycodone Hydrochloride)

TABLE 21

| | Rate of extraction into organic solvent % | | | | | | | |
|---|---|---|---|---|---|---|---|---|
| Organic solvent | Formulation Example 15 | Formulation Example 16 | Formulation Example 17 | Formulation Example 18 | Formulation Example 19 | Formulation Example 20 | Formulation Example 21 | Comparative Example 4 |
| Methanol | 59 | 34 | 31 | 29 | 29 | 18 | 31 | 72 |
| Ethanol | 45 | 31 | 22 | 13 | 15 | 5 | 10 | 26 |
| Isopropyl alcohol | 15 | NT | 6 | 3 | 3 | 2 | 3 | 11 |
| Acetone | 69 | 51 | 30 | 14 | 37 | 27 | 44 | 34 |

(Extractability of Tramadol Hydrochloride)

TABLE 22

| Organic solvent | Rate of extraction into organic solvent % | | |
|---|---|---|---|
| | Formulation Example 10 | Formulation Example 11 | Formulation Example 12 |
| Methanol | 51 | 37 | 35 |
| Ethanol | 36 | 21 | 17 |
| Isopropyl alcohol | 28 | 9 | 13 |
| Acetone | 42 | 34 | 40 |

(Example 6) Extractability of Drug into Various Aqueous Solutions and Organic Solvents

[Extraction Test Conditions]
Amount of the solvent for use in extraction: 10 mL
Extraction operation: A tablet or a broken tablet is placed in a glass beaker, to which 10 mL of the solvent for extraction is then added. The beaker is left standing for a predetermined period of time, and then, the mixture of the tablet and the solvent is stirred using a spatula. Cotton is placed in the mixture thus stirred, and the extract is collected via the absorbent cotton using a syringe (10 mL) equipped with an injection needle (18 G).

The concentration of the drug in the extract collected by the extraction operation is determined. The amount of the drug extracted from the tablet is calculated using the obtained quantification value to determine the rate of extraction (ratio of the amount of the drug extracted to the amount of the drug contained in one tablet).

The quantification of oxycodone was carried out under the conditions used in Example 3.

The quantification of hydrocodone bitartrate was carried out as follows.
Test Conditions (HPLC)
Detector: ultraviolet absorptiometer
(Measurement wavelength) hydrocodone bitartrate: 210 nm
Column: Symmetry C18 (4.6 mm I.D.×250 mm, particle size: 5.0 μm, Waters Corp.)
Column temperature: constant temperature around 30° C.
Mobile phase: 50 mmol/L potassium dihydrogen phosphate/acetonitrile (85:15), mixed solution supplemented with 0.02% triethylamine
Sample cooler temperature: constant temperature around 25° C.
Flow rate: approximately 1.5 mL per minute
Injection volume: 20 μL
Analysis time: 8 minutes In this Example, the formulations of Formulation Examples 13 and 14 of Example 3 were used in addition to the following formulation of Formulation Example 22.

Formulation Example 22

(Granules A)
Oxycodone hydrochloride (Mallinckrodt Pharmaceuticals), ethylcellulose (ETHOCEL STD100FP, The Dow Chemical Company), hypromellose acetate succinate (AQOAT AS-LF, AS-HF, Shin-Etsu Chemical Co., Ltd.), hypromellose (METOLOSE 90SH-100000SR, Shin-Etsu Chemical Co., Ltd.) and talc (Matsumura Sangyo Co., Ltd.) were mixed in a mortar. Triethyl citrate (CITROFLEX, Matsumura Shoji Co., Ltd.) was dissolved in purified water. Then, the solution was added to the mixture and kneaded therewith, and the resultant was loaded to an extrusion granulator (DOMEGRAN DG-L1, Fuji Paudal Co., Ltd., screen: 0.6 mm) and extruded. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.) to obtain granules A.

(Granules B)
Polyethylene oxide (POLYOX WSRN60K, The Dow Chemical Company), ethylcellulose (ETHOCEL STD100FP, The Dow Chemical Company) and sodium stearyl fumarate (PRUV, JRS Pharma) were mixed, compressed in a tableting machine and then screened in a cutting mill (Power Mill, Dalton Co., Ltd., screen: 10 mm square, φ2 mm) to obtain granules B.

(Granules C)
Microcrystalline cellulose (CEOLUS PH102, Asahi Kasei Chemicals Corp.), low-substituted hydroxypropylcellulose (L-HPC NBD-022, Shin-Etsu Chemical Co., Ltd.), hydroxypropylcellulose (HPC-SL, Nippon Soda Co., Ltd.) and sodium stearyl fumarate (PRUV, JRS Pharma) were mixed, compressed in a tableting machine and then screened in a cutting mill (Power Mill, Dalton Co., Ltd., screen: 10 mm square, φ2 mm) to obtain granules C.

(Tablet)
Granules A, granules B, granules C, microcrystalline cellulose (CEOLUS KG802, Asahi Kasei Chemicals Corp.), hydroxypropylcellulose (HPC-H fine powder, Nippon Soda Co., Ltd.) and sodium stearyl fumarate (PRUV, JRS Pharma) were mixed, and the mixed powder was compressed to obtain tablets.

As shown in Table 24, in all of the formulation examples, the rate of drug extraction into various aqueous solutions and organic solvents was low for intact tablets or crushed tablets.

TABLE 23

| Components | Formulation Example 22 (mg/tablet) |
|---|---|
| Triethyl citrate | 21.3 |
| Purified water | 117.06 |
| Binder | 138.36 |
| Oxycodone hydrochloride | 5 |
| Ethylcellulose STD 100 FP | 40 |
| METOLOSE 90SH-100000SR | 4 |
| Hypromellose acetate succinate LF | 50 |
| Hypromellose acetate succinate HF | 50 |
| Talc | 40 |
| Purified water | q.s. |
| Granules A | 210.3 |
| Polyethylene oxide | 140 |
| Ethylcellulose STD 100 FP | 21.78 |
| Sodium stearyl fumarate | 1.56 |
| Granules B | 163.3 |
| Microcrystalline cellulose PH102 | 35 |
| Low-substituted hydroxypropylcellulose | 155 |
| Hydroxypropylcellulose | 8 |
| Sodium stearyl fumarate | 2 |
| Granules C | 200 |
| Hydroxypropylcellulose HPC-H | 25 |
| Microcrystalline cellulose KG802 | 50 |
| Sodium stearyl fumarate | 10 |
| Total amount | 658.6 |

TABLE 24

| Solvent | Temperature | Formulation Example 13 Crushed tablet | Formulation Example 13 Tablet | Formulation Example 14 Crushed tablet | Formulation Example 14 Tablet | Formulation Example 22 Crushed tablet | Formulation Example 22 Tablet |
|---|---|---|---|---|---|---|---|
| Methanol | Room temperature | 38% | 28% | 19% | 19% | 38% | 33% |
| 90% aqueous methanol solution | Room temperature | 8% | NT | 14% | NT | 4% | NT |
| 60% aqueous methanol solution | Room temperature | 0% | NT | 4% | NT | 2% | NT |
| Ethanol | Room temperature | 18% | 6% | 15% | 12% | 21% | 9% |
| 90% aqueous ethanol solution | Room temperature | 5% | NT | 8% | NT | 4% | NT |
| 60% aqueous ethanol solution | Room temperature | 1% | NT | 5% | NT | 1% | NT |
| Isopropanol | Room temperature | 9% | 2% | 3% | 3% | 10% | 3% |
| Acetone | Room temperature | 47% | 26% | 41% | 43% | 42% | 23% |
| Diethyl ether | Room temperature | 3% | NT | 5% | NT | 8% | NT |
| Hexane | Room temperature | 0% | NT | 0% | NT | 0% | NT |
| Saline | Room temperature | 0% | 4% | 4% | 3% | 0% | 4% |
| Saline | 95° C. | 4% | NT | 3% | NT | 4% | NT |
| Purified water | Room temperature | 0% | 4% | 5% | 3% | 0% | 0% |
| Purified water | 95° C. | 3% | NT | 3% | NT | 2% | NT |
| Buffer solution pH2 | Room temperature | 10% | NT | 10% | NT | 5% | NT |
| Buffer solution pH4 | Room temperature | 5% | NT | 4% | NT | 0% | NT |
| Buffer solution pH6 | Room temperature | 0% | NT | 0% | NT | 0% | NT |
| Buffer solution pH8 | Room temperature | 0% | NT | 0% | NT | 0% | NT |
| 5% aqueous acetic acid solution | Room temperature | 0% | NT | 0% | NT | 0% | NT |
| 5% aqueous acetic acid solution | 95° C. | 4% | NT | 0% | NT | 6% | NT |
| Aqueous ammonia solution | Room temperature | 0% | NT | 2% | NT | 3% | NT |

(Example 7) Stability

Formulation Example 23

(Granules A)

Oxycodone hydrochloride trihydrate (Daiichi Sankyo Co., Ltd.), hypromellose acetate succinate (AQOAT AS-LF, AS-HF, Shin-Etsu Chemical Co., Ltd.), hypromellose (METOLOSE 90SH-100000SR, Shin-Etsu Chemical Co., Ltd.) and talc (Matsumura Sangyo Co., Ltd.) were mixed in a high-shear granulator (High-Speed Mixer, LFS-GS-1, Fukae Powtec Corp.). Triethyl citrate (CITROFLEX, Matsumura Shoji Co., Ltd.) was dissolved in purified water. Then, the solution was added to the mixture and kneaded therewith, and the resultant was loaded to an extrusion granulator (DOMEGRAN DG-L1, Fuji Paudal Co., Ltd., screen: 0.6 mm) and extracted. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.) to obtain granules A.

(Granules B)

Polyethylene oxide (POLYOX WSRN60K, The Dow Chemical Company), ethylcellulose (ETHOCEL STD100FP, The Dow Chemical Company) and sodium stearyl fumarate (PRUV, JRS Pharma) were mixed, compressed in a tableting machine and then screened in a cutting mill (Power Mill, Dalton Co., Ltd., screen: ϕ2 mm) to obtain granules B.

(Granules C)

Microcrystalline cellulose (CEOLUS PH102, Asahi Kasei Chemicals Corp.), low-substituted hydroxypropylcellulose (L-HPC NBD-022, Shin-Etsu Chemical Co., Ltd.), hydroxypropylcellulose (HPC-SL, Nippon Soda Co., Ltd.) and sodium stearyl fumarate (PRUV, JRS Pharma) were mixed, compressed in a tableting machine and then screened in a cutting mill (Power Mill, Dalton Co., Ltd., screen: ϕ2 mm) to obtain granules C.

(Tablet)

Granules A, granules B, granules C, microcrystalline cellulose (CEOLUS KG802, Asahi Kasei Chemicals Corp.), hydroxypropylcellulose (HPC-H fine powder, Nippon Soda Co., Ltd.) and sodium stearyl fumarate (PRUV, JRS Pharma) were mixed, and the mixed powder was compressed to obtain tablets.

Comparative Examples 5 and 6

Oxycodone hydrochloride trihydrate (Daiichi Sankyo Co., Ltd.), polyethylene oxide (POLYOX WSR303, The Dow Chemical Company), polyethylene glycol (macrogol 6000, NOF Corp.) and hypromellose (METOLOSE 90SH-100000SR, Shin-Etsu Chemical Co., Ltd.) (α-tocopherol (Riken Vitamin Co., Ltd.) was used in Comparative Example 5) were mixed in a mortar, and the mixture was loaded to an extruder (HAAK MINICTW, Thermo Fisher Scientific Inc.) and then heated to 120° C. to obtain an extrudate. The extrudate was cut using a cutter to obtain granules.

(Test): Stability test: Each formulation was placed in a glass bottle and preserved at 40° C./75% RH for 2 weeks with the bottle opened. After storage, related substances were measured.

(Test): Evaluation of related substances

Preparation of Test Solution 1. 0.015 mol/L sodium 1-heptane sulfonate solution (pH 2.5)
   1) 3.03 g of sodium 1-heptane sulfonate is weighed and dissolved by the addition of 1000 mL of water.
   2) Phosphoric acid is added dropwise to this solution to adjust the pH to 2.5.

2. Mobile phase: described in Test conditions
3. Sample dissolution solution: Japanese Pharmacopoeia 2nd fluid for dissolution test Test Conditions Detector: ultraviolet absorptiometer (measurement wavelength: 230 nm)
Column: Shim-pack XR-ODS (3.0 mm I.D.×50 mm, particle size: 2.2 μm, Shimadzu Corp.)
Column temperature: constant temperature around 40° C.
Mobile phase A: 0.015 mol/L sodium 1-heptane sulfonate solution (pH 2.5)
Mobile phase B: methanol
Solution sending conditions (system suitability and standard solution):

| Time (min) | Mobile phase A (Vol %) | Mobile phase B (Vol %) |
|---|---|---|
| 0 to 22 | 77 | 23 |

Solution sending conditions (sample solution): the concentration gradient is controlled by changing the mixing ratio of mobile phase A and mobile phase B as follows.

| Time (min) | Mobile phase A (Vol %) | Mobile phase B (Vol %) |
|---|---|---|
| 0 to 22 | 77 | 23 |
| 22 to 26 | 77 → 60 | 23 → 40 |
| 26 to 40 | 60 | 40 |
| 40 to 50 | 77 | 23 |

Flow rate: approximately 15 minutes as the retention time of oxycodone (approximately 0.5 mL per minute)
Sample cooler temperature: constant temperature around 5° C.
Injection volume: 5 μL
Analysis time: 22 minutes (system suitability and standard solution), 50 minutes (sample solution)
Time span of measurement: 2 to 22 minutes (system suitability and standard solution), 2 to 40 minutes (sample solution)

Preparation of Measurement Sample
1. Preparation of Sample Solution
   1) One tablet of each example is transferred to a 50-mL volumetric flask.
   2) Immediately after addition of approximately 50 mL of the sample dissolution solution, the mixture is vigorously mixed for 30 minutes or longer.
   3) This solution is filtered through a membrane filter having a pore size of 0.45 μm. The first 2 mL or more of the filtrate is discarded, and the subsequent filtrate is used as a sample solution.
2. Preparation of Standard Solution
   The sample solution is diluted by any of the following methods.
   In the Case of Using Whole Pipette
   1) 1 mL of the sample solution is accurately weighed using a whole pipette and transferred to a 100-mL volumetric flask.
   2) The amount of the solution is accurately adjusted to 100 mL by the addition of the sample dissolution solution to prepare a standard solution.
   In the Case of Using Diluter
   25 μL of the sample solution and 2475 μL of the sample dissolution solution are accurately weighed using a diluter, transferred to a test tube and well mixed to prepare a standard solution.

3. Preparation of Solution for Test for Required Detectability
   1) 1 mL of the standard solution is accurately weighed using a whole pipette and transferred to a 20-mL volumetric flask.
   2) The amount of the solution is accurately adjusted to 20 mL by the addition of the sample dissolution solution to prepare a solution for test for required detectability.

System Suitability

Test for required detectability: When the procedure is conducted with 5 μL of the solution for test for required detectability under the conditions described above, it is confirmed that the peak area of oxycodone in this solution is equivalent to 3.5 to 6.5% of the peak area of oxycodone in the standard solution.

System performance: When the procedure is conducted with 5 μL of the standard solution operated under the conditions described above, the number of theoretical plates and the symmetry factor of the peak of oxycodone are 2000 stages or more and 0.8 to 1.2, respectively.

System reproducibility: When the test is repeated 6 times with 5 μL of the standard solution under the conditions described above, the relative standard deviation of the peak area of oxycodone is 2.0% or less.

Quantification Limit
The quantification limit is 0.05%.

(Results)
As shown in Table 28, an increase in related substances after the stability test was observed in the formulation produced by the hot melt extrusion method according to the prescription free from the stabilizer α-tocopherol (Comparative Example 5). A marked increase in related substances was not observed in the formulation similarly produced according to the prescription containing α-tocopherol (Comparative Example 6). The formulation of Formulation 23, despite being free from the stabilizer, did not much increase the related substances and was stable, as with the formulation example produced by hot melt extrusion using α-tocopherol (Comparative Example 6).

TABLE 25

| Components | Formulation Example 23 (mg/tablet) |
|---|---|
| Triethyl citrate | 20 |
| Purified water | 110 |
| Binder | 130 |
| Oxycodone hydrochloride trihydrate | 5.77 |
| METOLOSE 90SH-100000SR | 2 |
| Hypromellose acetate succinate LF | 70 |
| Hypromellose acetate succinate HF | 70 |
| Talc | 20 |
| Purified water | q.s. |
| Granules A | 187.77 |
| Polyethylene oxide | 180 |
| Ethylcellulose STD 100 FP | 28 |
| Sodium stearyl fumarate | 2 |
| Granules B | 210 |
| Microcrystalline cellulose PH102 | 35.36 |
| Low-substituted hydroxypropylcellulose | 106.07 |
| Hydroxypropylcellulose | 7.07 |
| Sodium stearyl fumarate | 1.5 |
| Granules C | 150 |
| Hydroxypropylcellulose HPC-H | 25 |
| Microcrystalline cellulose KG802 | 50 |
| Sodium stearyl fumarate | 10 |
| Total amount | 632.77 |

TABLE 26

| Components | Comparative Example 5 (mg/tablet) |
| --- | --- |
| Oxycodone hydrochloride trihydrate | 5.77 |
| Polyethylene glycol macrogol 6000 | 14 |
| METOLOSE 90SH-100000SR | 14 |
| Polyethylene oxide | 68 |
| α-tocopherol | 0.1 |
| Granules | 101.87 |

TABLE 27

| Components | Comparative Example 6 (mg/tablet) |
| --- | --- |
| Oxycodone hydrochloride trihydrate | 5.77 |
| Polyethylene glycol macrogol 6000 | 14 |
| METOLOSE 90SH-100000SR | 14 |
| Polyethylene oxide | 68 |
| Granules | 101.77 |

TABLE 28

| Storage condition | Package form | Comparative Example 5 | Comparative Example 6 | Formulation Example 23 |
| --- | --- | --- | --- | --- |
| | | Related substance total (%) | | |
| Initial | — | 0.06 | 0.21 | 0.28 |
| 40° C./75% RH 2W | Bottle opened | 0.54 | 3.84 | 0.32 |

(Example 8) Drug Release Behavior of Tablet

Formulation Example 24

(Granules A)

Oxycodone hydrochloride trihydrate (Daiichi Sankyo Co., Ltd.), hypromellose acetate succinate (AQOAT AS-LF, AS-HF, Shin-Etsu Chemical Co., Ltd.), hypromellose (METOLOSE 90SH-100000SR, Shin-Etsu Chemical Co., Ltd.) and talc (Matsumura Sangyo Co., Ltd.) were mixed in a high-shear granulator (High-Speed Mixer, LFS-GS-1, Fukae Powtec Corp.). Triethyl citrate (CITROFLEX, Matsumura Shoji Co., Ltd.) was dissolved in purified water. Then, the solution was added to the mixture and kneaded therewith, and the resultant was loaded to an extrusion granulator (DOMEGRAN DG-L1, Fuji Paudal Co., Ltd., screen: 0.6 mm) and extruded. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.) to obtain granules A.

(Granules B)

Polyethylene oxide (POLYOX WSRN60K, The Dow Chemical Company), ethylcellulose (ETHOCEL STD100FP, The Dow Chemical Company) and sodium stearyl fumarate (PRUV, JRS Pharma) were mixed, compressed in a tableting machine and then screened in a cutting mill (Power Mill, Dalton Co., Ltd., screen: φ2 mm) to obtain granules B.

(Granules C)

Microcrystalline cellulose (CEOLUS PH102, Asahi Kasei Chemicals Corp.), low-substituted hydroxypropylcellulose (L-HPC NBD-022, Shin-Etsu Chemical Co., Ltd.), hydroxypropylcellulose (Nippon Soda Co., Ltd., HPC-SL) and sodium stearyl fumarate (PRUV, JRS Pharma) were mixed, compressed in a tableting machine and then screened in a cutting mill (Power Mill, Dalton Co., Ltd., screen: φ2 mm) to obtain granules C.

(Tablet)

Granules A, granules B, granules C, microcrystalline cellulose (CEOLUS KG802, Asahi Kasei Chemicals Corp.), hydroxypropylcellulose (HPC-H fine powder, Nippon Soda Co., Ltd.) and sodium stearyl fumarate (PRUV, JRS Pharma) were mixed, and the mixed powder was compressed to obtain tablets.

(Test Method)

The dissolution behavior of the formulation was evaluated under the following conditions.

[Test Conditions]

Test method: paddle method for dissolution test method
Test medium: purified water, 500 mL
Test medium temperature: 37.0° C.±0.5° C.
Paddle rotation speed: 50 rpm

[Preparation of Test Solution]

1. 0.015 mol/L sodium 1-heptane sulfonate solution (pH 2.5)
  1) 3.03 g of sodium 1-heptane sulfonate is weighed and dissolved by the addition of 1000 mL of water.
  2) Phosphoric acid is added dropwise to this solution to adjust the pH to 2.5.
2. Mobile phase: described in Test conditions
3. Sample dissolution solution: purified water
  Test Conditions (HPLC)

Detector: ultraviolet absorptiometer (measurement wavelength: 230 nm)
Column: Shim-pack XR-ODS (3.0 mm I.D.×50 mm, particle size: 2.2 μm, Shimadzu Corp.)
Column temperature: constant temperature around 50° C.
Mobile phase A: 0.015 mol/L sodium 1-heptane sulfonate solution (pH 2.5)
Mobile phase B: methanol
Solution sending conditions:

| Time (min) | Mobile phase A (Vol %) | Mobile phase B (Vol %) |
| --- | --- | --- |
| 0 to 10 | 74 | 26 |

Sample cooler temperature: constant temperature around 25° C.
Flow rate: approximately 7.5 minutes as the retention time of oxycodone (approximately 0.5 mL per minute)
Injection volume: 5 μL
Analysis time: 10 minutes (Preparation of Measurement Sample)

1. Preparation of Sample Solution
  1) One formulation of this example is placed in each of 6 vessels and tested under the test conditions described above (dissolution test).
  2) 5 mL of the dissolution medium is collected using a 10-mL syringe equipped with a cannula at prescribed times from the start of the dissolution test.
  3) After the sampling, 5 mL of a replacement fluid is added.
  4) Each collected dissolution medium is centrifuged (3000 rpm, 10 min., 20° C.)

5) Each centrifuged dissolution medium is filtered through a membrane filter having a pore size of 0.45 μm (EKICRODISC, material: HT-Tuffryn, diameter: 25 mm, manufactured by Pall Corp.).

6) The first 2 mL or more of the filtrate is discarded, and the subsequent filtrate is used as a sample solution.

2. Preparation of Standard Solution

1) Approximately 0.06 g of an oxycodone standard is precisely weighed and transferred to a 50-mL volumetric flask.

2) The oxycodone standard is dissolved by the addition of the sample dissolution solution to accurately make 50 mL.

3) 2 mL of this solution is accurately weighed and transferred to a 200-mL volumetric flask.

4) The amount of the solution is accurately adjusted to 200 mL by the addition of the sample dissolution solution to prepare standard solution I (Std1).

5) Steps 1) to 4) are repeated to prepare standard solution II (Std2).

(System Suitability)
System performance: When the procedure is conducted with 5 μL of standard solution I under the conditions described above, the symmetry factor and the number of theoretical plates of oxycodone are 0.8 to 1.2 and 2000 stages or more, respectively.
System reproducibility (repeated injection): When the test is repeated a total 6 times (3 times each) with 5 μL of standard solution I and 5 μL of standard solution II under the conditions described above, the relative standard deviation of the peak area of oxycodone calculated as the amount of the product taken is 2.0% or less.
System reproducibility (validation of the system): The ratio of the peak area of oxycodone calculated as the amount of standard solution I (Check-sample) taken to the average peak area of oxycodone calculated as the amount of the product taken in System reproducibility (repeated injection) is 96.0 to 104.0%.

(Results)
As shown in FIG. 1, the formulation of Formulation Example 24 exhibited an immediate dissolution profile.

TABLE 29

| Components | Formulation Example 24 (mg/tablet) |
| --- | --- |
| Triethyl citrate | 20 |
| Purified water | 110 |
| Binder | 130 |
| Oxycodone hydrochloride trihydrate | 5.77 |
| METOLOSE 90SH-100000SR | 2 |
| Hypromellose acetate succinate LF | 70 |
| Hypromellose acetate succinate HF | 70 |
| Talc | 20 |
| Purified water | q.s. |
| Granules A | 187.77 |
| Polyethylene oxide | 180 |
| Ethylcellulose STD 100 FP | 28 |
| Sodium stearyl fumarate | 2 |
| Granules B | 210 |
| Microcrystalline cellulose PH102 | 35 |
| Low-substituted hydroxypropylcellulose | 155 |
| Hydroxypropylcellulose | 8 |
| Sodium stearyl fumarate | 2 |
| Granules C | 200 |
| Hydroxypropylcellulose HPC-H | 25 |
| Microcrystalline cellulose KG802 | 50 |
| Sodium stearyl fumarate | 10 |
| Total amount | 682.77 |

(Example 9) Drug Release Behavior of Tablet

Formulation Example 25

(Granules A)
Oxycodone hydrochloride trihydrate (Daiichi Sankyo Co., Ltd.), hypromellose acetate succinate (AQOAT AS-LF, Shin-Etsu Chemical Co., Ltd.) and sodium carboxymethylcellulose (SUNROSE F1400MC, Nippon Paper Chemicals Co., Ltd.)) were mixed in a high-shear granulator (High-Speed Mixer, LFS-GS-1, Fukae Powtec Corp.). Triethyl citrate (CITROFLEX, Matsumura Shoji Co., Ltd.) was dissolved in purified water. Then, the solution was added to the mixture and kneaded therewith, and the resultant was loaded to an extrusion granulator (DOMEGRAN DG-L1, Fuji Paudal Co., Ltd., screen: 0.6 mm) and extruded. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.) to obtain granules A.

(Granules B)
Polyethylene oxide (The Dow Chemical Company, POLYOX WSRN60K), ethylcellulose (The Dow Chemical Company, ETHOCEL STD100FP) and sodium stearyl fumarate (JRS Pharma, PRUV) were mixed, compressed in a tableting machine and then screened in a cutting mill (Power Mill, Dalton Co., Ltd., screen: ϕ2 mm) to obtain granules B.

(Granules C)
Microcrystalline cellulose (Asahi Kasei Chemicals Corp., CEOLUS PH102), low-substituted hydroxypropylcellulose (Shin-Etsu Chemical Co., Ltd., L-HPC NB-022), hydroxypropylcellulose (Nippon Soda Co., Ltd., HPC-SL) and sodium stearyl fumarate (JRS Pharma, PRUV) were mixed to obtain granules C.

(Tablet)
Granules A, granules B, granules C and sodium stearyl fumarate (JRS Pharma, PRUV) were mixed, and the mixed powder was compressed to obtain tablets.

(Test Method)
The dissolution behavior of the formulation was evaluated under the same conditions as in Example 8.

(Results)
As shown in FIG. 2, the formulation of Formulation Example 25 exhibited an immediate dissolution profile.

TABLE 30

| Components | Formulation Example 25 (mg/tablet) |
| --- | --- |
| Triethyl citrate | 10 |
| Purified water | 130.3 |
| Binder | 140.3 |
| Oxycodone hydrochloride trihydrate | 5.77 |
| Sodium carboxymethylcellulose | 23.58 |
| Hypromellose acetate succinate LF | 70 |
| Purified water | q.s. |

TABLE 30-continued

| Components | Formulation Example 25 (mg/tablet) |
|---|---|
| Granules A | 109.35 |
| Polyethylene oxide | 180 |
| Ethylcellulose STD 100 FP | 28 |
| Sodium stearyl fumarate | 2 |
| Granules B | 210 |
| Microcrystalline cellulose PH102 | 174.43 |
| Low-substituted hydroxypropylcellulose | 174.43 |
| Hydroxypropylcellulose | 17.44 |
| Sodium stearyl fumarate | 3.7 |
| Granules C | 370 |
| Sodium stearyl fumarate | 10 |
| Total amount | 699.35 |

(Example 10) Drug Release Behavior of Tablet

Formulation Example 26

(Granules A)

Tramadol hydrochloride (PROTOCHEMICALS AG), hypromellose acetate succinate (AQOAT AS-LF, AS-HF, Shin-Etsu Chemical Co., Ltd.) and sodium carboxymethylcellulose (SUNROSE F1400MC, Nippon Paper Chemicals Co., Ltd.)) were mixed in a high-shear granulator (High-Speed Mixer, LFS-GS-1, Fukae Powtec Corp.). Triethyl citrate (CITROFLEX, Matsumura Shoji Co., Ltd.) was dissolved in purified water. Then, the solution was added to the mixture and kneaded therewith, and the resultant was loaded to an extrusion granulator (DOMEGRAN DG-L1, Fuji Paudal Co., Ltd., screen: 0.6 mm) and extruded. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.) to obtain granules A.

(Granules B)

Polyethylene oxide (POLYOX WARN60K, The Dow Chemical Company), ethylcellulose (ETHOCEL STD100FP, The Dow Chemical Company) and sodium stearyl fumarate (PRUV, JRS Pharma) were mixed, compressed in a tableting machine and then screened in a cutting mill (Power Mill, Dalton Co., Ltd., screen: φ2 mm) to obtain granules B.

(Granules C)

Microcrystalline cellulose (CEOLUS PH102, Asahi Kasei Chemicals Corp.), low-substituted hydroxypropylcellulose (L-HPC NBD-022, Shin-Etsu Chemical Co., Ltd.), hydroxypropylcellulose (HPC-SL, Nippon Soda Co., Ltd.) and sodium stearyl fumarate (PRUV, JRS Pharma) were mixed, compressed in a tableting machine and then screened in a cutting mill (Power Mill, Dalton Co., Ltd., screen: φ2 mm) to obtain granules C.

(Tablet)

Granules A, granules B, granules C and sodium stearyl fumarate (JRS Pharma, PRUV) were mixed, and the mixed powder was compressed to obtain tablets.

(Test Method)

[Preparation of Test Solution]

1. Solution A 1) 950 mL of water and 5 mL of perchloric acid are added to a beaker and stirred.

2) 3.5 mL of 28% ammonia water is added thereto, and the mixture is well stirred.

3) 41.5 mL of water is added thereto, and the mixture is well stirred.

4) The pH is measured to confirm that the pH falls within the range of 2.2±0.2.

5) If the pH falls outside this range, the pH is adjusted by the addition of 28% ammonia water.

2. Mobile phase: described in Test conditions

3. Sample dissolution solution: 0.1 mol/L (0.1 N) hydrochloric acid test solution

[Test Conditions (Dissolution Test)]

Test method: paddle method for dissolution test

Test solution: 0.1 mol/L (0.1 N) hydrochloric acid test solution, 900 mL

Test solution temperature: 37.0° C.±0.5° C.

Paddle rotation speed: 100 rpm

Test Conditions (UV)

Detector: ultraviolet absorptiometer (measurement wavelength: 273 nm and 300 nm)

[Preparation of Measurement Sample]

1. Preparation of Sample Solution

1) One formulation of this example is placed in each of 6 vessels and tested under the test conditions described above (dissolution test).

2) 15 minutes, 30 minutes and 60 minutes after the start of the dissolution test, 5 mL (HPLC) or 10 mL (UV) of the dissolution medium is collected using a 10-mL syringe equipped with a cannula.

3) After the sampling, 5 mL (HPLC) or 10 mL (UV) of a replacement fluid is added.

4) Each collected dissolution medium is centrifuged (3000 rpm, 10 min., 20° C.), and this supernatant is used as a sample solution.

2. Preparation of Standard Solution

1) Approximately 0.05 g of a tramadol bulk is precisely weighed and transferred to a 100-mL volumetric flask.

2) The bulk is dissolved by the addition of the sample dissolution solution to accurately make 100 mL.

3) 10 mL of this solution is accurately weighed and transferred to a 100-mL volumetric flask.

4) The amount of the solution is accurately adjusted to 100 mL by the addition of the sample dissolution solution to prepare a standard solution (Std).

[Test Conditions (HPLC)]

Detector: ultraviolet absorptiometer (measurement wavelength: 273 nm)

Column: Symmetry C8, Waters (3.9 mmφ×150 mm, 5 μm), Waters Corp.

Column temperature: room temperature

Mobile phase: Solution A/acetonitrile (770/230)

Sample cooler temperature: room temperature

Flow rate: approximately 2.0 mL per minute

Injection volume: 20 μL

Analysis time: 10 minutes

System Suitability (HPLC)

System reproducibility (repeated injection): When the test is repeated 6 times with 20 μL of the standard solution under the conditions described above, the relative standard deviation of the peak area of tramadol calculated as the amount of the product taken is 2.0% or less.

(Results)

As shown in FIG. 3, the formulation of Formulation Example 26 exhibited an immediate dissolution profile.

TABLE 31

| Components | Formulation Example 26 (mg/tablet) |
|---|---|
| Triethyl citrate | 30 |
| Purified water | 165 |
| | |
| Binder | 195 |
| Tramadol hydrochloride | 50 |
| Sodium carboxymethylcellulose | 50 |
| Hypromellose acetate succinate LF | 105 |
| Hypromellose acetate succinate HF | 105 |
| Purified water | q.s. |
| | |
| Granules A | 340 |
| Polyethylene oxide | 180 |
| Ethylcellulose STD 100 FP | 28 |
| Sodium stearyl fumarate | 2 |
| | |
| Granules B | 210 |
| Microcrystalline cellulose PH102 | 35.36 |
| Low-substituted hydroxypropylcellulose | 106.07 |
| Hydroxypropylcellulose | 7.07 |
| Sodium stearyl fumarate | 1.5 |
| | |
| Granules C | 150 |
| Microcrystalline cellulose KG802 | 50 |
| Sodium stearyl fumarate | 10 |
| | |
| Total amount | 760 |

(Example 11) Drug Release Behavior of Tablet

The formulation of Formulation Example 24 was used in evaluation.
(Test Method)
The dissolution behavior of the formulation was evaluated under the following conditions.
[Test Conditions]
Test method: paddle method for dissolution test method
Test medium: 0.01 N hydrochloric acid, 900 mL
Test medium temperature: 37.0° C.±0.5° C.
Paddle rotation speed: 50 rpm
The subsequent procedures were carried out under the same conditions as in Example 8.
(Results)
As shown in FIG. 4, the formulation of Formulation Example 24 exhibited an immediate dissolution profile.

(Example 12) Drug Release Behavior of Tablet

The formulation of Formulation Example 25 was used.
(Test Method)
The dissolution behavior of the formulation was evaluated under the following conditions.
[Test Conditions]
Test method: paddle method for dissolution test
Test medium: 0.01 N hydrochloric acid, 900 mL
Test medium temperature: 37.0° C.±0.5° C.
Paddle rotation speed: 50 rpm
The subsequent procedures were carried out in the same way as in Example 8.
(Results)
As shown in FIG. 5, the formulation of Formulation Example 25 exhibited an immediate dissolution profile.

(Example 13) Drug Release Behavior of Tablet

The formulation of Formulation Example 13 was used.
(Test Method)
The dissolution behavior of the formulation was evaluated under the following conditions.
[Test Conditions]
Test method: paddle method for dissolution test
Test medium: 0.01 N hydrochloric acid, 900 mL
Test medium temperature: 37.0° C.±0.5° C.
Paddle rotation speed: 50 rpm
The subsequent procedures were carried out in the same way as in Example 8.
(Results)
As shown in FIG. 6, the formulation of Formulation Example 13 exhibited an immediate dissolution profile.

(Example 14) Drug Release Behavior of Tablet

The formulation of Formulation Example 22 was used.
[Test Conditions]
Test method: paddle method for dissolution test
Test medium: 0.01 N hydrochloric acid, 900 mL
Test medium temperature: 37.0° C.±0.5° C.
Paddle rotation speed: 50 rpm
The subsequent procedures were carried out in the same way as in Example 8.
(Results)
As shown in FIG. 7, the formulation of Formulation Example 22 exhibited an immediate dissolution profile.

(Example 15) Drug Release Behavior of Tablet

Formulation Example 27

(Granules A)
Hydromorphone hydrochloride (Daiichi Sankyo Co., Ltd.), ethylcellulose (ETHOCEL STD100FP, The Dow Chemical Company), hypromellose acetate succinate (AQOAT AS-LF, AS-HF, Shin-Etsu Chemical Co., Ltd.), hypromellose (METOLOSE 90SH-100000SR, Shin-Etsu Chemical Co., Ltd.) and talc (Matsumura Sangyo Co., Ltd.) were mixed in a mortar. Triethyl citrate (CITROFLEX, Matsumura Shoji Co., Ltd.) was dissolved in purified water. Then, the solution was added to the mixture and kneaded therewith, and the resultant was loaded to an extrusion granulator (DOMEGRAN DG-L1, Fuji Paudal Co., Ltd., screen: 0.6 mm) and extruded. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.) to obtain granules A.
(Granules B)
Polyethylene oxide (POLYOX WSRN60K, The Dow Chemical Company), ethylcellulose (ETHOCEL STD100FP, The Dow Chemical Company) and sodium stearyl fumarate (PRUV, JRS Pharma) were mixed, compressed in a tableting machine and then screened in a cutting mill (Power Mill, Dalton Co., Ltd., screen: 10 mm square, φ2 mm) to obtain granules B.
(Granules C)
Microcrystalline cellulose (CEOLUS PH102, Asahi Kasei Chemicals Corp.), low-substituted hydroxypropylcellulose (L-HPC NBD-022, Shin-Etsu Chemical Co., Ltd.), hydroxypropylcellulose (HPC-SL, Nippon Soda Co., Ltd.) and sodium stearyl fumarate (PRUV, JRS Pharma) were mixed, compressed in a tableting machine and then screened in a cutting mill (Power Mill, Dalton Co., Ltd., screen: 10 mm square, φ2 mm) to obtain granules C.
(Tablet)
Granules A, granules B, granules C, microcrystalline cellulose (CEOLUS KG802, Asahi Kasei Chemicals Corp.), hydroxypropylcellulose (HPC-H fine powder, Nippon Soda Co., Ltd.) and sodium stearyl fumarate (PRUV, JRS Pharma) were mixed, and the mixed powder was compressed to obtain tablets.

[Test Conditions]
Test method: paddle method for dissolution test
Test medium: 0.01 N hydrochloric acid, 900 mL
Test medium temperature: 37.0° C.±0.5° C.
Paddle rotation speed: 50 rpm
Test Conditions (HPLC)
Detector: ultraviolet absorptiometer (measurement wavelength: 220 nm)
Column: Shim-pack XR-ODS (3.0 mm I.D.×50 mm, particle size: 2.2 μm, Shimadzu Corp.
Column temperature: constant temperature around 50° C.
Mobile phase A: 0.015 mol/L sodium 1-heptane sulfonate solution (pH 2.5)
Mobile phase B: methanol
Solution sending conditions:

| Time (min) | Mobile phase A (Vol %) | Mobile phase B (Vol %) |
| --- | --- | --- |
| 0 to 4 | 70 | 30 |

Sample cooler temperature: constant temperature around 25° C.
Flow rate: constant flow rate of 0.5 mL per minute (retention time of hydromorphone: approximately 2.5 minutes)
Injection volume: 10 μL
Analysis time: 4 minutes
(Results)
As shown in FIG. 8, the formulation of Formulation Example 27 exhibited an immediate dissolution profile.

TABLE 32

| Components | Formulation Example 27 (mg/tablet) |
| --- | --- |
| Triethyl citrate | 21.3 |
| Purified water | 117.06 |
| | |
| Binder | 138.36 |
| Hydromorphone hydrochloride | 4.51 |
| Ethylcellulose STD 100 FP | 40 |
| METOLOSE 90SH-100000SR | 4 |
| Hypromellose acetate succinate LF | 50 |
| Hypromellose acetate succinate HF | 50 |
| Talc | 40 |
| Purified water | q.s. |
| | |
| Granules A | 209.81 |
| Polyethylene oxide | 140 |
| Ethylcellulose STD 100 FP | 21.78 |
| Sodium stearyl fumarate | 1.56 |
| | |
| Granules B | 163.33 |
| Microcrystalline cellulose PH102 | 35 |
| Low-substituted hydroxypropylcellulose | 155 |
| Hydroxypropylcellulose | 8 |
| Sodium stearyl fumarate | 2 |
| | |
| Granules C | 200 |
| Hydroxypropylcellulose HPC-H | 25 |
| Microcrystalline cellulose KG802 | 50 |
| Sodium stearyl fumarate | 10 |
| | |
| Total amount | 658.13 |

(Example 16) Drug Release Behavior of Tablet

Formulation Example 28

(Granules A)

Oxycodone hydrochloride (Mallinckrodt Pharmaceuticals), polyethylene glycol (PEG6000, NOF Corp.), hypromellose acetate succinate (AQOAT AS-LF, Shin-Etsu Chemical Co., Ltd.), hypromellose (METOLOSE 90SH-100000SR, Shin-Etsu Chemical Co., Ltd.) and talc (Matsumura Sangyo Co., Ltd) were mixed in a mortar. Triethyl citrate (CITROFLEX, Matsumura Shoji Co., Ltd.) and hydroxypropylcellulose (HPC-L, Nippon Soda Co., Ltd.) were dissolved in purified water. Then, the solution was added to the mixture and kneaded therewith, and the resultant was loaded to an extrusion granulator (DOMEGRAN DG-L1, Fuji Paudal Co., Ltd., screen: 0.6 mm) and extruded. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.), and an ethylcellulose dispersion (AQUACOAT ECD30) supplemented with triethyl citrate (CITROFLEX, Matsumura Shoji Co., Ltd.) was sprayed to the resulting granules using a fluidized-bed granulator (Multiplex FD-MP-01, Powrex Corp.). The granules were dried to obtain granules A.

(Granules B)

Polyethylene oxide (POLYOX WSRN60K, The Dow Chemical Company), ethylcellulose (ETHOCEL STD100FP, The Dow Chemical Company) and sodium stearyl fumarate (PRUV, JRS Pharma) were mixed, compressed in a tableting machine and then screened in a cutting mill (Power Mill, Dalton Co., Ltd., screen: 10 mm square, φ2 mm) to obtain granules B.

(Granules C)

Microcrystalline cellulose (CEOLUS PH102, Asahi Kasei Chemicals Corp.), low-substituted hydroxypropylcellulose (L-HPC NBD-022, Shin-Etsu Chemical Co., Ltd.), hydroxypropylcellulose (HPC-SL, Nippon Soda Co., Ltd.) and sodium stearyl fumarate (PRUV, JRS Pharma) were mixed, compressed in a tableting machine and then screened in a cutting mill (Power Mill, Dalton Co., Ltd., screen: 10 mm square, φ2 mm) to obtain granules C.

(Tablet)

Granules A, granules B, granules C, microcrystalline cellulose (CEOLUS KG802, Asahi Kasei Chemicals Corp.), hydroxypropylcellulose (HPC-H fine powder, Nippon Soda Co., Ltd.) and sodium stearyl fumarate (PRUV, JRS Pharma) were mixed, and the mixed powder was compressed to obtain tablets.

(Test Method)

[Test Conditions]
Test method: paddle method for dissolution test
Test medium: Japanese Pharmacopoeia 2nd fluid for dissolution test, 900 mL
Test medium temperature: 37.0° C.±0.5° C.
Paddle rotation speed: 50 rpm The subsequent procedures were carried out in the same way as in Example 8.

(Results)

As shown in FIG. 9, the formulation of Formulation Example 28 released the drug slowly and exhibited an extended-release dissolution profile.

TABLE 33

| Components | Formulation Example 28 (mg/tablet) |
| --- | --- |
| Triethyl citrate | 32.34 |
| Ethylcellulose dispersion AQUACOAT ECD30 | 161.51 |
| Ethylcellulose as solid matter | 48.5 |
| Coating | 80.84 |
| Triethyl citrate | 22.4 |
| Hydroxypropylcellulose | 2 |
| Purified water | 123.2 |
| Binder | 147.6 |
| Oxycodone hydrochloride | 10 |
| Polyethylene glycol PEG6000 | 10 |
| Hypromellose acetate succinate HF | 149.2 |
| Purified water | q.s. |
| Granules A | 274.4 |
| Polyethylene oxide | 140 |
| Ethylcellulose STD 100 FP | 21.78 |
| Sodium stearyl fumarate | 1.56 |
| Granules B | 163.3 |
| Microcrystalline cellulose PH102 | 49 |
| Low-substituted hydroxypropylcellulose | 217 |
| Hydroxypropylcellulose | 11.2 |
| Sodium stearyl fumarate | 28 |
| Granules C | 280 |
| Hydroxypropylcellulose HPC-H | 25 |
| Microcrystalline cellulose KG802 | 50 |
| Sodium stearyl fumarate | 10 |
| Total amount | 802.7 |

(Example 17) Drug Release Behavior of Tablet

Formulation Example 29

(Granules A)

Oxycodone hydrochloride (Mallinckrodt Pharmaceuticals), ethylcellulose (ETHOCEL STD100FP, The Dow Chemical Company), hypromellose acetate succinate (AQOAT AS-LF, AS-HF, Shin-Etsu Chemical Co., Ltd.), hypromellose (METOLOSE 90SH-100000SR, Shin-Etsu Chemical Co., Ltd.) and talc (Matsumura Sangyo Co., Ltd) were mixed in a mortar. Triethyl citrate (CITROFLEX, Matsumura Shoji Co., Ltd.) was dissolved in purified water. Then, the solution was added to the mixture and kneaded therewith, and the resultant was loaded to an extrusion granulator (DOMEGRAN DG-L1, Fuji Paudal Co., Ltd., screen: 0.6 mm) and extruded. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.) to obtain granules A.

(Granules B)

Polyethylene oxide (POLYOX WSRN60K, The Dow Chemical Company), ethylcellulose (ETHOCEL STD100FP, The Dow Chemical Company) and sodium stearyl fumarate (PRUV, JRS Pharma) were mixed, compressed in a tableting machine and then screened in a cutting mill (Power Mill, Dalton Co., Ltd., screen: 10 mm square, φ2 mm) to obtain granules B.

(Granules C)

Microcrystalline cellulose (CEOLUS PH102, Asahi Kasei Chemicals Corp.), low-substituted hydroxypropylcellulose (L-HPC NBD-022, Shin-Etsu Chemical Co., Ltd.), hydroxypropylcellulose (HPC-SL, Nippon Soda Co., Ltd.) and sodium stearyl fumarate (PRUV, JRS Pharma) were mixed, compressed in a tableting machine and then screened in a cutting mill (Power Mill, Dalton Co., Ltd., screen: 10 mm square, φ2 mm) to obtain granules C.

(Tablet)

Granules A, granules B, granules C, microcrystalline cellulose (CEOLUS KG802, Asahi Kasei Chemicals Corp.), hydroxypropylcellulose (HPC-H fine powder, Nippon Soda Co., Ltd.), acetaminophen (Compap-L, Mallinckrodt Pharmaceuticals) and sodium stearyl fumarate (PRUV, JRS Pharma) were mixed, and the mixed powder was compressed to obtain tablets.

[Test Conditions]

Test method: paddle method for dissolution test
Test medium: 0.01 N hydrochloric acid, 900 mL
Test medium temperature: 37.0° C.±0.5° C.
Paddle rotation speed: 50 rpm
 Test Conditions (HPLC)
Oxycodone was quantified by the method of Example 8.
Acetaminophen was quantified as follows.
Detector: ultraviolet absorptiometer
Measurement wavelength: 295 nm
Column: Symmetry C18 (4.6 mm I.D.×250 mm, particle size: 5.0 μm, Waters Corp.)
Column temperature: constant temperature around 30° C.
Mobile phase: 50 mmol/L potassium dihydrogen phosphate/acetonitrile (85:15), mixed solution supplemented with 0.02% triethylamine
Sample cooler temperature: constant temperature around 25° C.
Flow rate: approximately 1.5 mL per minute
Injection volume: 20 μL
Analysis time: 8 minutes
 (Results)
As shown in FIG. 10, the formulation of Formulation Example 29 exhibited immediate dissolution of oxycodone and acetaminophen.

TABLE 34

| Components | Formulation Example 29 (mg/tablet) |
| --- | --- |
| Triethyl citrate | 21.3 |
| Purified water | 117.06 |
| Binder | 138.36 |
| Oxycodone hydrochloride | 5 |
| Ethylcellulose STD 100 FP | 40 |
| METOLOSE 90SH-100000SR | 4 |
| Hypromellose acetate succinate LF | 50 |
| Hypromellose acetate succinate HF | 50 |
| Talc | 40 |
| Purified water | q.s. |
| Granules A | 210.3 |
| Polyethylene oxide | 140 |
| Ethylcellulose STD 100 FP | 21.78 |
| Sodium stearyl fumarate | 1.56 |
| Granules B | 163.3 |
| Microcrystalline cellulose PH102 | 35 |
| Low-substituted hydroxypropylcellulose | 155 |
| Hydroxypropylcellulose | 8 |
| Sodium stearyl fumarate | 2 |
| Granules C | 200 |
| Hydroxypropylcellulose HPC-H | 25 |
| Acetaminophen Compap-L | 361.1 |
| Sodium stearyl fumarate | 10 |
| Total amount | 969.7 |

(Example 18) Drug Release Behavior of Tablet

The formulation of Formulation Example 14 was used.
(Test Method)
Test Conditions (Dissolution Test)
Test method: paddle method for dissolution test
Test medium: 0.01 N HCl, 900 mL
Test medium temperature: 37.0° C.±0.5° C.
Paddle rotation speed: 50 rpm
Test Conditions (HPLC)
Detector: ultraviolet absorptiometer
(Measurement wavelength) hydrocodone bitartrate: 210 nm
(Measurement wavelength) acetaminophen: 295 nm
Column: Symmetry C18 (4.6 mm I.D.×250 mm, particle size: 5.0 μm, Waters Corp.)
Column temperature: constant temperature around 30° C.
Mobile phase: 50 mmol/L potassium dihydrogen phosphate/acetonitrile (85:15), mixed solution supplemented with 0.02% triethylamine
Sample cooler temperature: constant temperature around 25° C.
Flow rate: approximately 1.5 mL per minute
Injection volume: 20 μL
Analysis time: 8 minutes
(Results)
As shown in FIG. 11, the formulation of Formulation Example 14 exhibited immediate dissolution of hydrocodone and acetaminophen.

(Example 19) Drug Release Behavior of Tablet

Formulation Example 30

(Granules A)
Hydrocodone bitartrate (Daiichi Sankyo Co., Ltd.), ethylcellulose (ETHOCEL STD100FP, The Dow Chemical Company), hypromellose acetate succinate (AQOAT AS-LF, AS-HF, Shin-Etsu Chemical Co., Ltd.), hypromellose (METOLOSE 90SH-100000SR, Shin-Etsu Chemical Co., Ltd.) and talc (Matsumura Sangyo Co., Ltd) were mixed in a mortar. Triethyl citrate (CITROFLEX, Matsumura Shoji Co., Ltd.) was dissolved in purified water. Then, the solution was added to the mixture and kneaded therewith, and the resultant was loaded to an extrusion granulator (DOME-GRAN DG-L1, Fuji Paudal Co., Ltd., screen: 0.6 mm) and extruded. Then, wet granules were obtained after spheronization by using Marumerizer (MARUMERIZER, Dalton Co., Ltd.). The wet granules were dried in a fluidized-bed granulator (Multiplex FD-MP-01, Powrex Corp.) to obtain granules A.
(Granules B)
Polyethylene oxide (POLYOX WSRN60K, The Dow Chemical Company), ethylcellulose (ETHOCEL STD100FP, The Dow Chemical Company) and sodium stearyl fumarate (PRUV, JRS Pharma) were mixed, compressed in a tableting machine and then screened in a cutting mill (Power Mill, Dalton Co., Ltd., screen: 10 mm square, φ2 mm) to obtain granules B.
(Granules C)
Microcrystalline cellulose (CEOLUS PH102, Asahi Kasei Chemicals Corp.), low-substituted hydroxypropylcellulose (L-HPC NBD-022, Shin-Etsu Chemical Co., Ltd.), hydroxypropylcellulose (HPC-SL, Nippon Soda Co., Ltd.) and sodium stearyl fumarate (PRUV, JRS Pharma) were mixed, compressed in a tableting machine and then screened in a cutting mill (Power Mill, Dalton Co., Ltd., screen: 10 mm square, φ2 mm) to obtain granules C.
(Tablet)
Granules A, granules B, granules C, microcrystalline cellulose (CEOLUS KG802, Asahi Kasei Chemicals Corp.), hydroxypropylcellulose (HPC-H fine powder, Nippon Soda Co., Ltd.), acetaminophen (Compap-L, Mallinckrodt Pharmaceuticals) and sodium stearyl fumarate (PRUV, JRS Pharma) were mixed to obtain a mixed powder for the first layer. Further, promethazine hydrochloride (Tokyo Chemical Industries Co., Ltd.), silicified microcrystalline cellulose (JRS Pharma), sodium croscarmellose (FMC Biopolymer) and magnesium stearate (Mallinckrodt Pharmaceuticals) were mixed to obtain a mixed powder for the second layer. Bilayer tablets were produced using these mixed powders.
(Test Method)
Test Conditions (Dissolution Test)
Test method: paddle method for dissolution test
Test medium: 0.01 N HCl, 900 mL
Test medium temperature: 37.0° C.±0.5° C.
Paddle rotation speed: 50 rpm
Test Conditions (HPLC)
Quantification of Hydrocodone Bitartrate and Acetaminophen
Detector: ultraviolet absorptiometer
(Measurement wavelength) hydrocodone bitartrate: 210 nm
(Measurement wavelength) acetaminophen: 295 nm
Column: Symmetry C18 (4.6 mm I.D.×250 mm, particle size: 5.0 μm, Waters Corp.)
Column temperature: constant temperature around 30° C.
Mobile phase: 50 mmol/L potassium dihydrogen phosphate/acetonitrile (85:15), mixed solution supplemented with 0.02% triethylamine
Sample cooler temperature: constant temperature around 25° C.
Flow rate: approximately 1.5 mL per minute
Injection volume: 20 μL
Analysis time: 8 minutes
Quantification of Promethazine Hydrochloride
Detector: ultraviolet absorptiometer
Measurement wavelength: promethazine hydrochloride: 220 nm
Column: L-column 2 ODS (4.6 mm I.D.×50 mm, particle size: 5.0 μm, Chemical Evaluation and Research Institute, Japan (CERI))
Column temperature: constant temperature around 40° C.
Mobile phase A: 25 mL phosphate buffer solution (pH 7.0)
Mobile phase B: acetonitrile
Solution sending conditions:

| Time (min) | Mobile phase A (Vol %) | Mobile phase B (Vol %) |
|---|---|---|
| 0 to 12 | 60 | 40 |

Sample cooler temperature: constant temperature around 25° C.
Flow rate: constant flow rate of 1.0 mL per minute
Injection volume: 50 μL
Analysis time: 12 minutes
(Results)
As shown in FIG. 12, the formulation of Formulation Example 30 exhibited immediate dissolution of hydrocodone, acetaminophen and promethazine.

TABLE 35

| Components | Formulation Example 30 (mg/tablet) |
|---|---|
| Triethyl citrate | 21.3 |
| Purified water | 117.06 |
| Binder | 138.36 |
| Hydrocodone bitartrate | 7.5 |
| Ethylcellulose STD 100 FP | 40 |
| METOLOSE 90SH-100000SR | 3 |
| Hypromellose acetate succinate LF | 50 |
| Hypromellose acetate succinate HF | 50 |
| Talc | 30 |
| Purified water | q.s. |
| Granules A | 201.8 |
| Polyethylene oxide | 140 |
| Ethylcellulose STD 100 FP | 21.78 |
| Sodium stearyl fumarate | 1.56 |
| Granules B | 163.3 |
| Microcrystalline cellulose PH102 | 8.75 |
| Low-substituted hydroxypropylcellulose | 38.75 |
| Hydroxypropylcellulose | 2 |
| Sodium stearyl fumarate | 0.5 |
| Granules C | 50 |
| Hydroxypropylcellulose HPC-H | 25 |
| Compap-L | 361.1 |
| Sodium stearyl fumarate | 10 |
| Total amount of first layer | 811.2 |
| Promethazine hydrochloride | 12.5 |
| Silicified Microcristaline celulose | 121.5 |
| Sodium croscarmellose | 15 |
| Magnesium stearate | 1 |
| Total amount of second layer | 150 |
| Total amount | 961.2 |

Formulation Examples

Hereinafter, formulation Examples using the technique of the present invention will be shown.

TABLE 36

| Components | Prescription Example 1 (mg/tablet) | Prescription Example 2 (mg/tablet) | Prescription Example 3 (mg/tablet) | Prescription Example 4 (mg/tablet) | Prescription Example 5 (mg/tablet) | Prescription Example 6 (mg/tablet) | Prescription Example 7 (mg/tablet) |
|---|---|---|---|---|---|---|---|
| Triethyl citrate | 19 | 12.67 | 25.33 | 19 | 19 | 19 | 19 |
| Purified water | 105 | 70 | 140 | 105 | 105 | 105 | 105 |
| Binder | 124 | 82.67 | 165.33 | 124 | 124 | 124 | 124 |
| Hydrocodone bitartrate | 7.5 | 5 | 10 | 5 | 10 | 7.5 | 7.5 |
| Ethylcellulose STD 100 FP | 40 | 26.67 | 53.33 | 40 | 40 | 40 | 40 |
| METOLOSE 90SH-100000SR | 3 | 2 | 4 | 3 | 3 | 3 | 3 |
| Hypromellose acetate succinate LF | 50 | 33.33 | 66.67 | 50 | 50 | 50 | 50 |
| Hypromellose acetate succinate HF | 50 | 33.33 | 66.67 | 50 | 50 | 50 | 50 |
| Talc | 30 | 20 | 40 | 30 | 30 | 30 | 30 |
| Purified water | q.s. | q.s. | q.s. | q.s. | q.s. | q.s. | q.s. |
| Granules A | 199.5 | 133 | 266 | 197 | 202 | 199.5 | 199.5 |
| Polyethylene oxide WSR N-60K | 140 | 140 | 140 | 140 | 140 | — | — |
| Polyethylene oxide WSR-301 | — | — | — | — | — | 70 | — |
| Polyethylene oxide WSR-303 | — | — | — | — | — | — | 50 |
| Ethylcellulose STD 100 FP | 21.78 | 21.78 | 21.78 | 21.78 | 21.78 | 21.78 | 21.78 |
| Sodium stearyl fumarate | 1.56 | 1.56 | 1.56 | 1.56 | 1.56 | 1.56 | 1.56 |
| Granules B | 163.3 | 163.3 | 163.3 | 163.3 | 163.3 | 93.3 | 73.3 |
| Microcrystalline cellulose PH102 | 8.75 | 8.75 | 8.75 | 8.75 | 8.75 | 8.75 | 8.75 |
| Low-substituted hydroxypropylcellulose | 38.75 | 38.75 | 38.75 | 38.75 | 38.75 | 38.75 | 38.75 |
| Hydroxypropylcellulose | 2 | 2 | 2 | 2 | 2 | 2 | 2 |
| Sodium stearyl fumarate | 0.5 | 0.5 | 0.5 | 0.5 | 0.5 | 0.5 | 0.5 |
| Granules C | 50 | 50 | 50 | 50 | 50 | 50 | 50 |
| Hydroxypropylcellulose HPC-H | 25 | 25 | 25 | 25 | 25 | 50 | 50 |
| Acetaminophen Compap-L | 361.1 | 361.1 | 361.1 | 361.1 | 361.1 | 361.1 | 361.1 |
| Sodium stearyl fumarate | 10 | 10 | 10 | 10 | 10 | 10 | 10 |
| Total amount of first layer | 808.9 | 742.4 | 875.4 | 806.4 | 811.4 | 763.9 | 743.9 |
| Promethazine hydrochloride | 12.5 | 12.5 | 12.5 | 12.5 | 12.5 | 12.5 | 12.5 |
| Silicified Microcristaline cellulose | 121.5 | 121.5 | 121.5 | 121.5 | 121.5 | 121.5 | 121.5 |
| Sodium croscarmellose | 15 | 15 | 15 | 15 | 15 | 15 | 15 |
| Magnesium stearate | 1 | 1 | 1 | 1 | 1 | 1 | 1 |
| Total amount of second layer | 150 | 150 | 150 | 150 | 150 | 150 | 150 |
| Total amount | 958.9 | 892.4 | 1025.4 | 956.4 | 961.4 | 913.9 | 893.9 |

TABLE 37

| Components | Prescription Example 8 (mg/tablet) | Prescription Example 9 (mg/tablet) | Prescription Example 10 (mg/tablet) | Prescription Example 11 (mg/tablet) | Prescription Example 12 (mg/tablet) | Prescription Example 13 (mg/tablet) | Prescription Example 14 (mg/tablet) |
|---|---|---|---|---|---|---|---|
| Triethyl citrate | 21.3 | 14.20 | 28.40 | 21.3 | 21.3 | 21.3 | 21.3 |
| Purified water | 117.06 | 78.04 | 156.08 | 117.06 | 117.06 | 117.06 | 117.06 |

TABLE 37-continued

| Components | Prescription Example 8 (mg/tablet) | Prescription Example 9 (mg/tablet) | Prescription Example 10 (mg/tablet) | Prescription Example 11 (mg/tablet) | Prescription Example 12 (mg/tablet) | Prescription Example 13 (mg/tablet) | Prescription Example 14 (mg/tablet) |
|---|---|---|---|---|---|---|---|
| Binder | 138.36 | 92.24 | 184.48 | 138.36 | 138.36 | 138.36 | 138.36 |
| Hydrocodone bitartrate | 7.5 | 5 | 10 | 5 | 10 | 7.5 | 7.5 |
| Ethylcellulose STD 100 FP | 40 | 26.67 | 53.33 | 40 | 40 | 40 | 40 |
| METOLOSE 90SH-100000SR | 3 | 2 | 4 | 3 | 3 | 3 | 3 |
| Hypromellose acetate succinate LF | 50 | 33.33 | 66.67 | 50 | 50 | 50 | 50 |
| Hypromellose acetate succinate HF | 50 | 33.33 | 66.67 | 50 | 50 | 50 | 50 |
| Talc | 30 | 20 | 40 | 30 | 30 | 30 | 30 |
| Purified water | q.s. | q.s. | q.s. | q.s. | q.s. | q.s. | q.s. |
| Granules A | 201.8 | 134.5 | 269.1 | 199.3 | 204.3 | 201.8 | 201.8 |
| Polyethylene oxide WSR N-60K | 140 | 140 | 140 | 140 | 140 | — | — |
| Polyethylene oxide WSR-301 | — | — | — | — | — | 70 | — |
| Polyethylene oxide WSR-303 | — | — | — | — | — | — | 50 |
| Ethylcellulose STD 100 FP | 21.78 | 21.78 | 21.78 | 21.78 | 21.78 | 21.78 | 21.78 |
| Sodium stearyl fumarate | 1.56 | 1.56 | 1.56 | 1.56 | 1.56 | 1.56 | 1.56 |
| Granules B | 163.3 | 163.3 | 163.3 | 163.3 | 163.3 | 93.3 | 73.3 |
| Microcrystalline cellulose PH102 | 8.75 | 8.75 | 8.75 | 8.75 | 8.75 | 8.75 | 8.75 |
| Low-substituted hydroxypropylcellulose | 38.75 | 38.75 | 38.75 | 38.75 | 38.75 | 38.75 | 38.75 |
| Hydroxypropylcellulose | 2 | 2 | 2 | 2 | 2 | 2 | 2 |
| Sodium stearyl fumarate | 0.5 | 0.5 | 0.5 | 0.5 | 0.5 | 0.5 | 0.5 |
| Granules C | 50 | 50 | 50 | 50 | 50 | 50 | 50 |
| Hydroxypropylcellulose HPC-H | 25 | 25 | 25 | 25 | 25 | 50 | 50 |
| Acetaminophen Compap-L | 361.1 | 361.1 | 361.1 | 361.1 | 361.1 | 361.1 | 361.1 |
| Sodium stearyl fumarate | 10 | 10 | 10 | 10 | 10 | 10 | 10 |
| Total amount of first layer | 811.2 | 743.9 | 878.5 | 808.7 | 813.7 | 766.2 | 746.2 |
| Promethazine hydrochloride | 12.5 | 12.5 | 12.5 | 12.5 | 12.5 | 12.5 | 12.5 |
| Silicified Microcrystaline cellulose | 121.5 | 121.5 | 121.5 | 121.5 | 121.5 | 121.5 | 121.5 |
| Sodium croscarmellose | 15 | 15 | 15 | 15 | 15 | 15 | 15 |
| Magnesium stearate | 1 | 1 | 1 | 1 | 1 | 1 | 1 |
| Total amount of second layer | 150 | 150 | 150 | 150 | 150 | 150 | 150 |
| Total amount | 961.2 | 893.9 | 1028.5 | 958.7 | 963.7 | 916.2 | 896.2 |

INDUSTRIAL APPLICABILITY

The present invention can provide a pharmaceutical composition having abuse deterrent properties that possesses both a physical barrier and a chemical barrier and thereby prevent abuse by an abuser.

The invention claimed is:

1. An abuse deterrent formulation that resists being abused by an abuser, the abuse deterrent formulation comprising at least 3 types of granules (A) to (C):
    (A) granules comprising a co-granulated mixture of a pharmacologically active drug, a cellulosic polymer and a plasticizer, the granules having a property of having mechanical strength against pulverization;
    (B) granules comprising a component that exhibits viscosity after dispersion in an aqueous solution; and
    (C) granules comprising a component that disintegrates the formulation.

2. The abuse deterrent formulation according to claim 1, wherein the cellulosic polymer is hypromellose acetate succinate, ethylcellulose or hypromellose phthalate, and the plasticizer is triethyl citrate or triacetin.

3. The abuse deterrent formulation according to claim 1, wherein the component that exhibits viscosity is a water-soluble polymer whose viscosity is not influenced by ionic strength.

4. The abuse deterrent formulation according to claim 3, wherein the water-soluble polymer whose viscosity is not influenced by ionic strength is one or more members selected from hydroxypropylcellulose, hypromellose, polyvinyl alcohol, xanthan gum, guar gum, pectin, and polyethylene oxide.

5. The abuse deterrent formulation according to claim 3, wherein the water-soluble polymer whose viscosity is not influenced by ionic strength is polyethylene oxide.

6. The abuse deterrent formulation according to claim 1, wherein the granules (B) further comprise a hydrophobic additive that promotes the disintegration of tablets.

7. The abuse deterrent formulation according to claim 6, wherein the hydrophobic additive is ethylcellulose.

8. The abuse deterrent formulation according to claim 1, wherein the component that disintegrates the formulation is a disintegrant.

9. The abuse deterrent formulation according to claim 8, wherein the disintegrant is low-substituted hydroxypropylcellulose.

10. The abuse deterrent formulation according to claim 1, wherein the formulation further comprises a semi-natural water-soluble polymer.

11. The abuse deterrent formulation according to claim 10, wherein the semi-natural water-soluble polymer is sodium carboxymethylcellulose.

12. The abuse deterrent formulation according to claim 1, wherein the formulation further comprises a polymer that exhibits viscosity when dissolved in an organic solvent.

13. The abuse deterrent formulation according to claim 12, wherein the polymer that exhibits viscosity when dissolved in an organic solvent is hydroxypropylcellulose.

14. The abuse deterrent formulation according to claim 1, wherein the pharmacologically active drug is a narcotic analgesic, an opioid analgesic or a psychotropic.

15. The abuse deterrent formulation according to claim 1, wherein the pharmacologically active drug is hydromorphone or a salt thereof, hydrocodone or a salt thereof, oxycodone or a salt thereof, or tramadol or a salt thereof.

16. The abuse deterrent formulation according to claim 1, wherein the dosage form is an oral solid dosage form.

17. The abuse deterrent formulation according to claim 1, wherein the dosage form is a tablet.

18. The abuse deterrent formulation according to claim 17, wherein the formulation exhibits immediate release.

19. The abuse deterrent formulation according to claim 17, wherein the formulation exhibits extended release.

20. The abuse deterrent formulation according to claim 19, wherein the formulation comprises the granules (A) provided with a coating.

21. The abuse deterrent formulation according to claim 20, wherein the coating is made of a coating base composed of ethylcellulose.

22. The abuse deterrent formulation according to claim 1, comprising at least 3 types of granules (A) to (C):
(A) granules comprising hydromorphone or a salt thereof, a cellulosic polymer selected from hypromellose acetate succinate, ethylcellulose, and hypromellose phthalate, and a plasticizer selected from triethyl citrate and triacetin;
(B) granules comprising one or more of hydroxypropylcellulose, hypromellose, polyvinyl alcohol, xanthan gum, guar gum, pectin, and polyethylene oxide; and
(C) granules comprising low-substituted hydroxypropylcellulose.

23. The abuse deterrent formulation according to claim 22, comprising at least 3 types of granules (A) to (C):
(A) granules comprising hydromorphone or a salt thereof, hypromellose acetate succinate, and triethyl citrate;
(B) granules comprising polyethylene oxide; and
(C) granules comprising low-substituted hydroxypropylcellulose.

24. The abuse deterrent formulation according to claim 1, comprising at least 3 types of granules (A) to (C):
(A) granules comprising hydrocodone or a salt thereof, a cellulosic polymer selected from hypromellose acetate succinate, ethylcellulose, and hypromellose phthalate, and a plasticizer selected from triethyl citrate and triacetin;
(B) granules comprising one or more of hydroxypropylcellulose, hypromellose, polyvinyl alcohol, xanthan gum, guar gum, pectin, and polyethylene oxide; and
(C) granules comprising low-substituted hydroxypropylcellulose.

25. The abuse deterrent formulation according to claim 24, comprising at least 3 types of granules (A) to (C):
(A) granules comprising hydrocodone or a salt thereof, hypromellose acetate succinate, and triethyl citrate;
(B) granules comprising polyethylene oxide; and
(C) granules comprising low-substituted hydroxypropylcellulose.

26. The abuse deterrent formulation according to claim 1, comprising at least 3 types of granules (A) to (C):
(A) granules comprising oxycodone or a salt thereof, a cellulosic polymer selected from hypromellose acetate succinate, ethylcellulose, and hypromellose phthalate, and a plasticizer selected from triethyl citrate and triacetin;
(B) granules comprising one or more of hydroxypropylcellulose, hypromellose, polyvinyl alcohol, xanthan gum, guar gum, pectin, and polyethylene oxide; and
(C) granules comprising low-substituted hydroxypropylcellulose.

27. The abuse deterrent formulation according to claim 26, comprising at least 3 types of granules (A) to (C):
(A) granules comprising oxycodone or a salt thereof, hypromellose acetate succinate, and triethyl citrate;
(B) granules comprising polyethylene oxide; and
(C) granules comprising low-substituted hydroxypropylcellulose.

28. The abuse deterrent formulation according to claim 1, comprising at least 3 types of granules (A) to (C):
(A) granules comprising tramadol or a salt thereof, a cellulosic polymer selected from hypromellose acetate succinate, ethylcellulose, and hypromellose phthalate, and a plasticizer selected from triethyl citrate and triacetin;
(B) granules comprising one or more of hydroxypropylcellulose, hypromellose, polyvinyl alcohol, xanthan gum, guar gum, pectin, and polyethylene oxide; and
(C) granules comprising low-substituted hydroxypropylcellulose.

29. The abuse deterrent formulation according to claim 28, comprising at least 3 types of granules (A) to (C):
(A) granules comprising tramadol or a salt thereof, hypromellose acetate succinate, and triethyl citrate;
(B) granules comprising polyethylene oxide; and
(C) granules comprising low-substituted hydroxypropylcellulose.

30. A method for treating cancer pain or psychiatric disease, comprising administering to a subject in need thereof an effective amount of the abuse deterrent formulation according to claim 1.

* * * * *